United States Patent
Savakis et al.

(10) Patent No.: US 6,225,121 B1
(45) Date of Patent: *May 1, 2001

(54) EUKARYOTIC TRANSPOSABLE ELEMENT

(75) Inventors: Charalambos Savakis, Crete (GR); Gerald H. Franz, Baden (AT); Athanasios Loukeris, Heidelberg (DE); Apostolos G. Klinakis, Crete (GR)

(73) Assignee: Institute of Molecular Biology and Biotechnology/FORTH, Crete (GR)

( * ) Notice: Subject to any disclaimer, the term of this patent is extended or adjusted under 35 U.S.C. 154(b) by 0 days.

This patent is subject to a terminal disclaimer.

(21) Appl. No.: 09/067,755

(22) Filed: Apr. 27, 1998

Related U.S. Application Data

(63) Continuation-in-part of application No. 08/530,566, filed on Sep. 20, 1995, now Pat. No. 5,840,865, which is a continuation-in-part of application No. 08/239,765, filed on May 9, 1994, which is a division of application No. 07/946,237, filed on Sep. 14, 1992, now Pat. No. 5,348,874.

(51) Int. Cl.$^7$ ............................. C12N 5/00; C12N 15/85; C12N 15/87
(52) U.S. Cl. .................... 435/440; 435/455; 435/456; 435/462; 435/465
(58) Field of Search ................. 435/440, 455, 435/456, 462, 463, 183, 194, 325, 320.1; 536/23.1, 23.2, 23.5

(56) References Cited

U.S. PATENT DOCUMENTS

| | | | |
|---|---|---|---|
| 5,348,874 | 9/1994 | Savakis et al. | 435/196 |
| 6,051,430 | 4/2000 | Plasterk et al. | 435/462 |

FOREIGN PATENT DOCUMENTS

| | | |
|---|---|---|
| WO 97/29202 | 8/1997 | (WO) . |
| WO 99/07871 | 2/1999 | (WO) . |

OTHER PUBLICATIONS

"D.hydei minos transposon–like element encoding transposase," submitted to EMBL Data Library by Charalambos Savakis; Released by EMBL Data Library on Sep. 12, 1991.

Franz, G. et al., "Minos, a new transposable element from *Drosophila hydei*, is a member of the Tc1–like family of transposons," *Nucleic Acids Research*, 19 (23):6646 (1991).

Franz, G. et al., "Mobile Minos elements from *Drosophila hydei* encode a two–exon transposase with similarity to the paired DNA–binding domain," *Proc. Natl. Acad. Sci. USA*, 91:4746–4750 (1994).

Loukeris, T. G. et al., "Gene transfer into the Medfly, *Ceratitis capitata*, with a *Drosophila hydei* transposable element," *Science*, 270:2002–2005 (1995).

Loukeris, T. G. et al., "Introduction of the transposable element Minos into the germ line of *Drosophila melanogaster*," *Proc. Natl. Acad. Sci. USA*, 92:9485–9489 (1995).

Arcà, B. et al., "Mobilization of a Minos transposon in *Drosophila melanogaster* chromosomes and chromatid repair by heteroduplex formation," *Genetics* 145:267–279 (1997).

Ivics, Z. et al., "Molecular reconstruction of Sleeping Beauty, a Tc1–like transposon from fish, and its transposition in human cells," *Cell* , 91:501–510 (1997).

Gueiros–Filho, F. J. et al., "Trans–kingdom transposition of the Drosophila element mariner within the protozoan Leishmania," *Science*, 276:1716–1719 (1997).

Marshall, A., "The insects are coming," *Nature Biotechnology*, 16:530–533 (1998).

Spradling, A. C. et al., "Gene disruptions using P transposable elements: An integral component of the Drosophila genome project," *Proc. Natl. Acad. Sci. USA*, 92: 10824–10830 (1995).

Bellen, H. J. et al., "P–element–mediated enhancer detection: A versatile method to study development in Drosophila," *Genes &Development* 3:1288–1300 (1989).

Wilson, C. et al., "P–element–mediated enhancer detection: An efficient method for isolating and characterizing developmentally regulated genes in Drosophilla," *Genes &Development* 3:1301–1313 (1989).

Chambers, C. A., "TKO'ed: Lox, stock and barrel," *BioEssays*, 16(12):865–868 (1994).

Kidwell, M. G., "Voyage of an ancient mariner," *Nature*, 362:202 (1993).

Plasterk, R. H. A., "Molecular mechanisms of transposition and its control," *Cell*, 74:781–786 (1993).

Kaufman, P. D. and Rio, D.C., "P element transposition in vitro proceeds by a cut–and–paste mechanism and uses GTP as a cofactor," *Cell*, 69:27–39 (1992).

Bainton, R. et al., "Tn7 transposition in vitro proceeds through an excised transposon intermediate generated by staggered breaks in DNA," *Cell*, 65:805–816 (1991).

(List continued on next page.)

Primary Examiner—Nashaat T. Nashed
(74) Attorney, Agent, or Firm—Hamilton, Brook, Smith & Reynolds, P.C.

(57) ABSTRACT

Disclosed are isolated transposable elements, or isolated DNA sequences which encode a transposase protein (or a portion of a transposase protein). The isolated transposable elements or the isolated DNA sequences being characterized by the ability to hybridize to the DNA sequence of Minos-1. The invention also relates to a purified transposase protein, or peptide fragments thereof, encoded by such DNA sequences. Such transposable are useful in methods for the stable introduction of a DNA sequence of interest into a cell. The invention further relates to transgenic animals, gene tagging and insertional mutagenesis produced by such methods. The sequence information disclosed herein is useful in the design of oligonucleotide primers which are useful for the isolation of related members of the Tc-1 family of transposable elements.

45 Claims, 9 Drawing Sheets

OTHER PUBLICATIONS

Bainton, R. J. et al., "Tn7 transposition: Target DNA recognition is mediated by multiple Tn7-encoded proteins in a purified in vitro System," *Cell*, 72:931–943 (1993).

Lam, W. L. et al., "Discovery of amphibian Tc1–like transposon families," *J. Mol. Biol.*, 257:359–366 (1996).

Russell, S. H. et al., "Directed excision of a transgene from the plant genome," *Mol. Genet. Genet.*, 234:49–59 (1992).

Gu, H. et al., "Independent control of immunoglobulin switch recombination at individual switch regions evidenced through Cre–loxP–mediated gene targeting," *Cell*, 73:1155–1164 (1993).

Robertson, H.M., et al., "Recent horizontal transfer of a mariner transposable element amoung and between Diptera and Neuroptera", *Mol. Biol. Evol.,* 12(5):850–862 (1995).

Coates, C.J., et al., "The transposable element mariner can excise in non–drosophilid insects", *Mol. Gen. Genet*, 249:246–252 (1995).

Lozovskaya, E.R., et al., "Germline transformation of *Drosophila virilis* mediated by the transposable element hobo", *Genetics*, 142:173–177 (1996).

O'Brochta, D.A. et al., "Transposable elements and gene transformation in non–Drosophilid insects", *Insect Biochem. Molec. Biol.*, 26:739–753 (1996).

Vos, J.C., et al., "Transposase is the only nematode protein required for in vitro transposition of Tc1", *Genes &Development*, 10:755–761 (1996).

Pinkerton, A.C., et al., "Mobility of hAT transposable elements in the Old World bollworm, *Helicoverpa armigera*", *Insect Molecular Biology*, 5(4):223–2227 (1996).

Robertson, H.M. et al., "A mariner transposable element from a lacewing", *Nucleic Acids Research*, 20(23):6405 (1992).

```
acgagcccaaccactattaattcgaacagcatgttttttgcagtgcgcaatgtttaa    60
cacactatattatcaatactactaaagataacacataccaatgcattcgtctcaaagag  120
aatttattctcttcacgacgaaaaaaagtttgctctattccaacaacaacaaaaa       180
tatgagtaatttattcaaacgtttgcttaagagataagaaaaagtgaccactattaat   240
tcgaacgcgcgtaaGCTTACCTTAATCTCAAGAGCAAAACAAAAGCAACTAATGTA     300
ACGGAATCATTATCTAGTTATGATCTGCAAATAATGTCACAATACAGCATGCAAAAAAAT 360
TTTAGATTGCTGCAGATCAGTAGAAGTTTAGCAACGATGGTTCGTGGTAAACCTATTCT  420
AAAGAAATCAGAGTATTGATTAGGGATTATTTTAAATCTGGAAAGACACTTACGGAGATA 480
AGCAAGCAATTAAAATTTGCCTAAGTCGTCTCTGTGCATGGGGTGATACAAATTTCAAAAAAA 540
AATGGGAATATTGAAAATAACATTGCGAATAGAGGCCGAACATCAGCAATAACACCCCGC 600
GACAAAAGACAACTGGCCAAAATTGTTAAGGCTGATCGTCGCCAATCTTTGAGAAATTTG 660
```

FIG. 1A

```
GCTTCTAAGTGGTCGCAGCAATTGGCAAAACTGTCAAGCGAGAGTGGACGCGACAAATTA      720

AAAAGTATTGGATATGGTTTTTATAAgtatgtttgtattacctgtgcatcgtaccca         780 ataacttactcgtaatcttactcgtagGCCAAGGAAAAACCCTTGCTTACGCTTCGTCAA      840
                                       *
AAAAAGAAGCGTTTGCAATGGGCTCGGGAAAGGATGTCTTGGACTCAAAGGCAATGGGAT      900
                                                         A
ACCATCATATTCAGGCGATGAAGCTAAATTTGATGTTAGTGTCGGCGATACGAGAAAACGC     960

GTCATCCGTAAGAGGTCAGAAACATACCATAAAGACTGCCTAAAAGAACAACAAAGTTT      1020

CCTGCGAGCACTATGGTATGGGATGTATGTCTGCCAAAGGATTAGGAAAACTTCATTTC      1080

ATTGAAGGGACAGTTAATGCTGAAAAATATATTAATATTTTACAAGATAGTTTGTTGCCA     1140

TCAATACCAAAACTATCAGATTGCGGTGAATTCACTTTTCAGCAGGACGGAGCATCATCG    1200
                      T
                      ıc
CACACAGCCAAGCGAACCAAAAATTGGCTGCAATATAATCAAATGGAGGTTTTAGATTGG    1260
```

FIG. 1B

```
CCATCAAATAGTCCAGATCTAAGCCCCAATTGAAAATATTTGGTGGCTAATGAAAAACCAG      1320
CTTCGAAATGAGCCACAAAGGAATATATTTCTGACTTGAAAATCAAGTTGCAAGAGATGTGG     1380
GACTCAATTTCTCAAGAGCATTGCAAAAATTTGTTAAGCTCAATGCCAAAACGAGTTAAA       1440
TGCGTAATGCAGGCCAAGGGCGACGTTACACACAATTCTAATATTAATTAAATTATTGTTT      1500
AAGTATGATAGTAAATCACAttacgccgcgttcgaattaatagtggtcactttttctta        1560
tctcttaagcaaaccgtttgaataattactcatattttgttgtgttggaaatagagc          1620
aaaactttttttcgtcgtgaagagaataaaattctctttgagacgaaatgcattggta         1680
tgtgttatcttagtagtagtattgatatagtgtgttaaacattgcgcactgcaaaaaa         1740
acatgctgttcgaattaatagtggttggggctcgt   1775
```

FIG. 1C

```
acgagcccaaccactattaattcgaacagcatgtttttttgcagtgcgcaatgtttaa                      60
cacactatattcataatactaaagataacacataccaatgcattcgtctcaaagag                       120
aattttattctcttcacgacgaaaaaaagttttgctctattccaacaacaacaaaaa                      180
tatgagtaattattcaaacggtttgcttaagagataagaaaaagtgaccactattaat                     240
tcgaacgcggcgtaaGCTTACCTTAATCTCAAGAAGCAAAACAAAAGCAACTAATGTA                     300
ACGGAATCATTATCTAGTTATGATCTGCAAATAATGTCACAATACAGCATGCAAAAAAAT                   360
                   M  V  R  G  K  P  I  S                                       8
TTTAGAATTGCTGCAGATCAGTAGAAGTTTAGCAACGATGGTTCGTGGTAAACCTATTTC                   420
 K  E  I  R  V  L  I  R  D  Y  F  K  S  G  K  T  L  T  E  I                    28
TAAAGAAATCAGAGTATTGATTAGGGATTATTTTAAATCTGGAAAGACACTTACGGAGAT                   480
 S  K  Q  L  N  L  P  K  S  S  V  H  G  V  I  Q  I  F  K  K                    48
AAGCAAGCAATTAAATTGCCTAAGTCGTCTGTGCATGGGGTGATACAAATTTTCAAAAA                    540
 N  G  N  I  E  N  N  I  A  N  R  G  R  T  S  A  I  T  P  R                    68
AAATGGGAATATTGAAAATAACATTGCGAATAGAGGCCGAACATCAGCAATAACACCCCG                   600
 D  K  R  Q  L  A  K  I  V  K  A  D  R  R  Q  S  L  R  N  L                    88
CGACAAAAGACAACTGGCCAAAATTGTTAAGGCTGATCGTCGCCAATCTTTGAGAAATTT                   660
 A  S  K  W  S  Q  T  I  G  K  T  V  K  R  E  W  T  R  Q  Q                   108
GGCTTCTAAGTGGTCGCAGACAATTGGCAAAACTGTCAAGCGAGAGTGGACGCGACAGCA                   720
 L  K  S  I  G  Y  G  F  Y  K                                                 118
ATTAAAAAGTATTGGATATGGTTTTTATAAAgtatgtttgttattacctgtgcatcgta                    780
                                  A  K  E  K  P  L  L  T  L  R               128
cccaataacttactcgtaatcttactcgtagGCCAAGGAAAAACCCTTGCTTACGCTTCG                   840
```

FIGURE 2A

```
                                                                                *
Q   K   K   K   R   L   Q   W   A   R   E   R   M   S   W   T   Q   R   Q   W    148
TCAAAAAAGAAGCGTTTGCAATGGGCTCGGGAAAGGATGTCTTGGACTCAAAGGCAATG                      900
                                                                          A

D   T   I   I   F   S   D   E   A   K   F   D   V   S   V   G   D   T   R   K    168
GGATACCATCATATTCAGCGATGAAGCTAAATTTGATGTTAGTGTCGGCGATACGAGAAA                     960

R   V   I   R   K   R   S   E   T   Y   H   K   D   C   L   K   R   T   T   K    188
ACGCGTCATCCGTAAGAGGTCAGAAACATACCATAAAGACTGCCTAAAAGAACAACAAA                     1020

F   P   A   S   T   M   V   W   G   C   M   S   A   K   G   L   G   K   L   H    208
GTTTCCTGCGAGCACTATGGTATGGGGATGTATGTCTGCCAAAGGATTAGGAAAACTTCA                    1080

F   I   E   G   T   V   N   A   E   K   Y   I   N   I   L   Q   D   S   L   L    228
TTTCATTGAAGGGACAGTTAATGCTGAAAAATATATTTTACAAGATAGTTTGTT                          1140
                                    L
P   S   I   P   K   L   S   D   C   G   E   F   T   F   Q   Q   D   G   A   S    248
GCCATCAATACCAAAACTATCAGATTGCGGTGAATTCACTTTTCAGCAGGACGGAGCATC                    1200
                    T
S   H   T   A   K   R   T   K   N   W   L   Q   Y   N   Q   M   E   V   L   D    268
ATCGCACACAGCCAAGCGAACCAAAAATTGGCTGCAATATAATCAAATGGAGGTTTTAGA                    1260

W   P   S   N   S   P   D   L   S   P   I   E   N   I   W   L   M   K   N        288
TTGGCCATCAAATAGTCCAGATCTAAGCCCCAATTGAAAATATTTGGTGGCTAATGAAAAA                   1320

Q   L   R   N   E   P   Q   R   N   I   S   D   L   K   I   K   L   Q   E   M    308
CCAGCTTCGAAATGAGCCACAAAGGAATATTTCTGACTTGAAAATCAAGTTGCAAGAGAT                    1380

W   D   S   I   S   Q   E   H   C   K   N   L   L   S   S   M   P   K   R   V    328
GTGGGACTCAATTTCTCAAGAGCATTGCAAAAATTTGTTAAGCTCAATGCCAAAACGAGT                    1440

K   C   V   M   Q   A   K   G   D   V   T   Q   F                                341
TAAATGCGTAATGCAGGCCAAGGGCGACGTTACACAATTCTAATATTAATTAAATTATTG                    1500

FIGURE 2B
```

```
TTTTAAGTATGATAGTAAATCACAttacgccgcgttcgaattaatagtggtcactttttt    1560
cttatctcttaagcaaaccgtttgaataaattactcatattttgttgttgttggaaata    1620
gagcaaaactttttttcgtcgtgaagagaataaattctctttgagacgaaatgcatt      1680
ggtatgtgttatctttagtagtattgatatatagtgtgttaaacattgcgcactgcaaa    1740
aaaaacatgctgttcgaattaatagtggtggggctcgt  1779
```

FIGURE 2C

EUKARYOTIC TRANSPOSABLE ELEMENT

RELATED APPLICATIONS

This application is a continuation-in-part of U.S. Ser. No. 08/530,566, filed Sep. 20, 1995, now U.S. Pat. No. 5,840,865 which is a continuation-in-part of U.S. Ser. No. 08/239,765, filed May 9, 1994, which is a divisional of U.S. Ser. No. 07/946,237, filed Sep. 14, 1992 (now U.S. Pat. No. 5,348,874), the entire teachings of which are incorporated herein by reference.

BACKGROUND OF THE INVENTION

The Tc1-like family of transposons and the retroviral-like transposons are unique for their wide dispersion in diverse organisms. Members belonging to the Tc-1-like family have been characterized in nematodes, diptera, fish and amphibians: Tc1 in *Caenorhabditis elegans,* TCb1 in *Caenorhabditis briggsae,* HB1 in *Drosophila melanogaster,* Uhu in *Drosophila heteroneura,* Minos in *Drosophila hydei,* and Tes1 in the Pacific hagfish *Eptatetrus stouti.* All are characterized by a relative short length (1.6 to 1.8 kb), the presence of inverted terminal repeats, and significant sequence similarity in the region between the repeats.

The Minos-1 transposable element has been identified as a 1775 bp dispersed repetitive sequence inserted within the transcribed spacer in one of the repeats of *Drosophila hydei* (Franz and Savakis, *Nucl. Acids Res.* 19: 6646 (Dec. 11, 1991)). The element is characterized by 255-bp long perfect inverted repeats and the presence of two long, non-overlapping open reading frames (ORFs) on the same strand. The longest of the ORFs shows approximately 30% sequence identity with TcA, but does not begin with an ATG codon. It appears, therefore, that the cloned element represents a defective member of the Minos family, as is the case with all previously sequenced Tc1-like elements, with the possible exceptions of Tc1 and Tcb1.

Transposable elements are natural components of genomes ranging from bacteria to vertebrate organisms (Lewin, *Genes VI,* Chapter 18, Oxford University Press, (1997)). Thus, due to their widespread phylogenetic distribution, evolutionary conservation and genomic mobility, transposons are valuable tools for genetic manipulations, such as, for example, the integration of nucleic acids in germ cells for the production of transgenic animals, and genetic transformation and insertional mutagenesis in somatic cells and viral vectors for use as therapeutics.

SUMMARY OF THE INVENTION

The invention relates to an isolated transposable element, or an isolated DNA sequence which encodes a transposase protein (or a portion of a transposase protein). The isolated transposable element or the isolated DNA sequence is characterized by the ability to hybridize to the DNA sequence of Minos 1 under stringent hybridization conditions. The invention also relates to a purified transposase protein, or peptide fragments thereof, encoded by such DNA sequences.

In another aspect, the invention relates to a method for the stable introduction of a nucleic acid sequence of interest into a cell. This method involves the use of an isolated transposable element of the type described in the preceding paragraph, the isolated transposable element being modified to include the nucleic acid sequence of interest flanked by the termini of the isolated transposable element. This modified transposable element is introduced into the cell in the presence of a transposase protein, or a nucleic acid sequence or a virus encoding a transposase protein. The role of the transposase protein is to catalyze the transposition of the modified transposable element containing the nucleic acid sequence of interest into the genome of the cell. Also envisioned are cells produced by this method.

In a third aspect, the invention relates to a method for isolating members of the Tc-1 family of transposable elements from genomic DNA of a eukaryote of interest. According to this method, oligonucleotide primers are provided which are complementary to a sequence of at least about 12 consecutive nucleotides which encode amino acids which are highly conserved in aligned sequences of nematode Tc-1 family members and Minos family members. These oligonucleotide primers are used to prime amplification by the polymerase chain reaction (PCR). The amplification products are then used to isolate DNA encoding the entire Tc-1 family member from the eukaryote of interest by conventional methods.

In a fourth aspect, the invention relates to a transgenic animal. The transgenic animal is produced by a method which involves the use of an isolated transposable element characterized by the ability to hybridize to the DNA sequence of Minos 1, the isolated transposable element being modified to include the nucleic acid sequence of interest flanked by the termini of the isolated transposable element. This modified transposable element is introduced into a cell in the presence of a transposase protein, or a DNA sequence or a virus encoding a transposase protein.

In a fifth aspect, the invention relates to methods of integrating a nucleic acid sequence of interest into a chromosome of a cell. This method involves the use of an isolated transposable element of the type described in the preceding paragraph, the isolated transposable element being modified to include the nucleic acid sequence of interest flanked by the termini of the isolated transposable element. This modified transposable element is introduced into the cell in the presence of a transposase protein, or a nucleic acid sequence or a virus encoding a transposase protein. Also envisioned are cells produced by this method.

In a sixth aspect, the invention relates to a transgenic plant. The transgenic plant is produced by a method which involves the use of an isolated transposable element characterized by the ability to hybridize to the DNA sequence of Minos-1, the isolated transposable element being modified to include the nucleic acid sequence of interest flanked by the termini of the isolated transposable element. This modified transposable element is introduced into a plant cell in the presence of a transposase protein, or a nucleic acid sequence or a virus encoding a transposase protein.

In a seventh aspect, the invention relates to insertional mutagenesis and gene tagging. In this approach, the Minos-transposable elements are inserted into a nucleic acid (e.g., a gene) to induce a mutation in the nucleic acid which produces a phenotypic alteration. The location of the nucleic acid is identified by the presence of the Minos transposon sequence. The Minos transposon sequence can be identified, for example, using standard molecular hybridization techniques, such as in situ hybridization, Southern blotting, and colony hybridization. The terms "transposable element" and "transposon" are used interchangeably herein.

In a particular embodiment, this aspect of the invention relates to methods for inducing a mutation of interest in a cell (a Minos transposon-induced mutation), and identifying and isolating a gene of interest which includes the mutation from the cell. The methods involve a the use of an isolated transposable element of the type described above which is introduced into a cell in the presence of a transposase protein, or a nucleic acid sequence or a virus encoding the transposase protein. In a particular embodiment, the transposable element is modified to include a promoter operably linked to an indicator gene (such as a reporter gene or a selectable marker gene) flanked by the inverted terminal repeats of the isolated transposable element. In a further embodiment, expression of the indicator gene is detected, thereby identifying cells in which the transposable element has integrated into the genome of the cells. Cells which have a mutation of interest can then identified and selected by looking for a particular phenotype conferred by the mutation but not the corresponding endogenous gene. These cells are referred to herein as cells including a Minos transposon-induced (or Minos transposable element-induced) mutation. The location of the gene which includes the mutation can then be identified by the presence of the Minos transposon sequence and then isolated.

In a second embodiment, this aspect of the invention relates to methods for selecting an insertional mutation in a gene (a Minos transposon-induced mutation). The methods comprise introducing a transposable element of the type described above, modified to include a minimal promoter or a splice acceptor site operably linked to an indicator gene flanked by the inverted terminal repeats of the isolated transposable element, into a population of cells in the presence of a transposase protein, or a nucleic acid sequence or a virus encoding the transposase protein. Expression of the indicator gene is detected, thereby identifying cells in which the transposable element has integrated near or within a particular gene in the cells. These cells are also referred to herein as cells including a Minos transposon-induced (or Minos transposable element-induced) mutation. The location of the gene in which the transposable element has integrated near or within is identified by the presence of the Minos transposon sequence and then isolated.

In an eighth aspect, the invention relates to methods for reversing a Minos transposon-induced mutation in a cell. The methods comprise introducing a transposase protein, or a nucleic acid sequence or a virus encoding a transposase protein, into cells identified as including a Minos transposon-induced mutation, as described herein. The transposase protein catalyzes reversion of the Minos transposon-induced mutation. Cells in which reversion of the mutation has occurred can be identified, for example, by looking for loss of a particular phenotype conferred by the mutation or for absence of the product encoded by the indicator gene.

In a ninth aspect, the invention relates to a method for introducing a reversible mutation in a gene of interest in a cell. In a particular embodiment, this method involves the use of a Minos transposable element modified to include a promoter operably linked to an indicator gene flanked by the inverted terminal repeats of the isolated transposable element. In a second embodiment, this method involves the use of a Minos transposable element modified to include a minimal promoter operably linked to an indicator gene flanked by the inverted terminal repeats of the isolated transposable element. In a third embodiment, the method involves the use of a Minos transposable element modified to include a splice acceptor site operably linked to an indicator gene flanked by the inverted terminal repeats of the isolated transposable element. The modified transposable element is introduced into a gene of interest, thereby producing a mutated gene. The mutated gene is introduced into a sample of cells under conditions sufficient for homologous recombination between the mutated gene and the endogenous gene. Thus, in this aspect of the invention, the gene of interest is a gene which has sufficient sequence homology to the endogenous gene in which a reversible mutation is to be introduced, for homologous recombination between the endogenous gene and the mutated gene. Cells in which the endogenous gene has been replaced with the mutated gene can then identified and selected by looking for a particular phenotype conferred by the mutated gene, for loss of a particular phenotype conferred by the endogenous gene or for presence of a product encoded by the indicator gene. The mutation in the gene introduced in accordance with the present method can be reversed by a method comprising introducing a transposase protein, or a nucleic acid sequence or a virus encoding a transposase protein, into cells in which the endogenous gene has been replaced with the mutated gene. Cells in which reversion of the mutation has occurred can be identified, for example, by looking for loss of a particular phenotype conferred by the mutated gene, for a particular phenotype conferred by the endogenous gene or for absence of the product encoded by the indicator gene.

In a tenth aspect, the invention relates to a method for inducing loss of a nucleic acid sequence of interest integrated into the chromosome of a cell. In a particular embodiment, the nucleic acid sequence of interest refers to a gene of interest. The method comprises introducing a transposase protein, or a nucleic acid sequence or a virus encoding a transposase protein, into cells identified as including a nucleic acid sequence of interest which was integrated into the chromosome of a cell using an isolated Minos transposable element of the type described above. Cells in which loss of the nucleic acid sequence of interest has occurred can be identified, for example, by looking for loss of a particular phenotype conferred by the nucleic acid sequence of interest or for absence of the product encoded by an indicator gene.

BRIEF DESCRIPTION OF THE DRAWINGS

FIGS. 1A–1C is a diagram providing the consensus sequence of elements Minos-1, Minos-2 and Minos-3 with nucleotide deletions after nucleotides 365, 678 and 715. The terminal inverted repeats and the intron sequence are shown in small letters. Differences between the three elements are indicated above and below the nucleotide sequence. More specifically, nucleotide 896 is a G in Minos-2 and Minos-3 and an A in Minos-1. Nucleotide 1157 is a C in Minos-1 and Minos-3 and a T in Minos-2.

FIG. 2A–2C is a diagram providing the consensus sequence of elements Minos-1, Minos-2 and Minos-3. The terminal inverted repeats and the intron sequence are shown in small letters. The first and last nucleotides of the sequence, A and T, respectively, are generated by a duplication of the chromosomal target site TA during insertion of the element. The deduced amino acid sequence of two open reading frames is shown above the nucleotide sequence. Differences between the three elements are indicated above and below the nucleotide sequence. More specifically, nucleotide 900 is a G in Minos-2 and Minos-3 and an A in Minos-1. Nucleotide 1161 is a C in Minos-1 and Minos-3 and a T in Minos-2. Amino acid residue 148 is a tryptophan in Minos-2 and Minos-3 and a stop codon in Minos-1. Amino acid residue 235 is a serine in Minos-1 and Minos-3 and a leucine in Minos-2.

SEQUENCE LISTING CROSS-REFERENCE

Figure 3A:
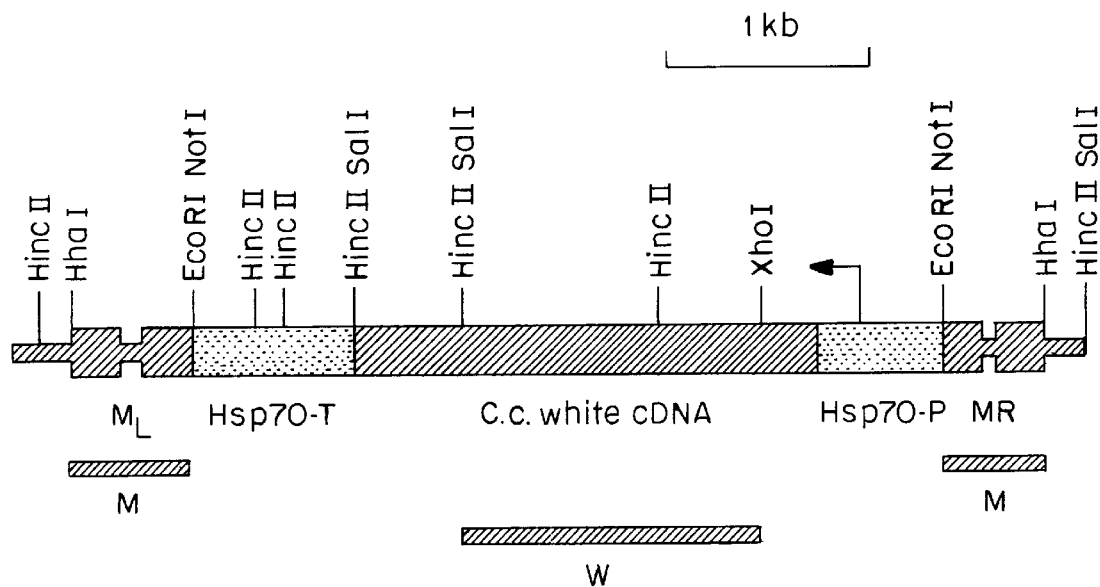
FIG. 3A is a diagram of the insert of the transposon plasmid pMihsCcw. ML and MR signify the left- and right-end parts of Minos, respectively. Hatched boxes indicate the *D. melanogaster* Hsp70 promoter (Hsp70-P) and terminator (Hsp70-T) sequences. Black bars indicate the Minos (M) and Medfly white (W) sequences that were used as probes for the analysis of transformants.

In portions of the Specification, the following sequence listing cross-reference is applicable:

SEQ ID NO: 1 Nucleic acid sequence of Minos-1 with nucleotide deletions after nucleotides 365, 678 and 715.

SEQ ID NO: 2 Nucleic acid sequence of Minos-2 with nucleotide deletions after nucleotides 365, 678 and 715.

SEQ ID NO: 3 Nucleic acid sequence of Minos-3 with nucleotide deletions after nucleotides 365, 678 and 715.

SEQ ID NO: 4 Nucleic acid sequence of Minos-1.
SEQ ID NO: 5 Deduced amino acid sequence of Minos-1.
SEQ ID NO: 6 Nucleic acid sequence of Minos-2.
SEQ ID NO: 7 Deduced amino acid sequence of Minos-2.
SEQ ID NO: 8 Nucleic acid sequence of Minos-3.
SEQ ID NO: 9 Deduced amino acid sequence of Minos-3.
SEQ ID NO: 10 MVWGC.
SEQ ID NO: 11 WPSQSPDL.
SEQ ID NO: 12 WPSNSPDL.

DETAILED DESCRIPTION OF THE INVENTION

The invention disclosed herein is based on the initial discovery of Minos-1, an apparently defective member of the Tc-1 family of transposable elements. This 1779-bp element is characterized by perfect inverted repeats of 255-bp at each termini. The sequence encodes two non-overlapping reading frames, one of which has significant similarity with the putative transposase encoded by the transposable element Tc1 of *Caenorhabiditis elegans*. However, the Minos-1 element, because of a stop codon within the putative transposase gene, apparently cannot encode an active transposase.

In an effort to identify sequences related to the Minos-1 sequence, genomic DNA of *D. hydei* was probed with a portion of the Minos-1 sequence under stringent hybridization conditions. As discussed in detail in the Examples section which follows, two full-length related sequences were identified, both of which encode an active transposase.

ISOLATED NUCLEIC ACIDS AND USES THEREOF

Thus, in one aspect, the subject invention relates to an isolated transposable element which hybridizes to the DNA sequence of Minos-1 under stringent hybridization conditions. As used herein, stringent hybridization conditions are considered to be hybridization in a buffered solution of 0.9 M NaCl at 55° C. In *D. hydei* there are up to 30-copies detected which hybridize to Minos thus, it is likely that a large number of variants can be isolated using these conditions. Comparable hybridization stringency can be established at other salt concentrations and temperatures. This is accomplished, for example, by the inclusion of organic denaturants such as formamide in the hybridization buffer. Nucleic acid sequences which hybridize to the Minos-1 sequence under stringent hybridization conditions are referred to herein as members of the Minos family of transposable elements. Nucleic acid sequences which hybridize to the Minos-1 sequence under stringent hybridization conditions include, for example, the Minos-2 and Minos-3 DNA sequences. Other examples of nucleic acid sequences which hybridize to the Minos-1 sequence under stringent hybridization conditions include Minos-1, Minos-2 and Minos-3 DNA sequences having base deletions, insertions and/or substitutions.

The term transposable element, as used herein, refers to a DNA sequence whose excision from/insertion into genomic DNA is catalyzed by a functional transposase protein encoded by a non-defective member of the Minos family of transposable elements. A member of the Minos family which encodes a functional transposase and possesses other necessary cis-acting elements (e.g., inverted terminal repeats) falls within this definition. In addition, a transposable element which encodes a defective transposase (e.g., Minos-1 itself) falls within this definition. As discussed in greater detail below, such defective transposable elements can be used in conjunction with a helper element (e.g., a member of the Minos family which encodes a functional transposase) to introduce a nucleic acid sequence of interest into a cell (e.g, a eukaryotic cell such as an animal, plant or yeast cell or a prokaryotic cell such as a bacterial cell).

The invention also relates to an isolated DNA sequence encoding a functional transposase protein, or a portion of a transposase protein, encoded by a member of the Minos family. Such a DNA sequence need not retain the ability to transpose in the presence of the encoded transposase protein. A sequence encoding a functional transposase protein can be used to prepare an expression construct which can be used to produce the transposase protein by recombinant DNA methodology. Such a recombinant protein can be over-produced in a eukaryotic (e.g., yeast) or prokaryotic host cell (e.g., E. coli), and subsequently purified by conventional methods.

The active transposase can be used in a variety of ways. For example, as discussed below, the transposase can be co-introduced into a eukaryotic cell with a modified transposon carrying a nucleic acid sequence of interest to catalyze the insertion of the modified transposon into the genomic DNA of the eukaryotic cell. This is an alternative to the co-introduction of a helper construct in eukaryotic cells which do not constitutively produce the Minos transposase.

In addition, the transposase, or portions thereof, can be used to produce antibodies (monoclonal and polyclonal) reactive with the transposase protein. Methods for the production of monoclonal and polyclonal antibodies are straightforward once a purified antigen is available.

Through the isolation and DNA sequence analysis of additional members of the Minos family, refinement of the consensus sequence of FIGS. 2A–2C is possible. This refined consensus sequence can be used to predict modifications of the transposase protein which will affect the specific activity of the transposase. Such predictions are easily tested by modifying the DNA sequence of an expression construct encoding the transposase by site-directed mutagenesis to either bring the sequence into a greater degree of conformance with the consensus sequence, or a lesser degree of conformance with the consensus sequence. The affect of such changes on the activity of the transposase protein are monitored by assessing the affect of the mutation on transposition frequency catalyzed by the recombinant transposase.

METHODS FOR THE INTRODUCTION OF NUCLEIC ACID SEQUENCES INTO A CELL

Transposable elements of the Minos family, and the active transposase encoded by such elements, are useful in methods for introducing a nucleic acid sequence of interest into a cell (e.g., a eukaryotic cell, such as an animal, plant or yeast cell or a prokaryotic cell, such as a bacterial cell). Typically, the nucleic acid sequence of interest will be a gene which encodes a protein. Such a gene can be placed under the regulatory control of a promoter which can be induced or repressed, thereby offering a greater degree of control with respect to the level of the protein in the cell. As used herein, the term "promoter" refers to a sequence of DNA, usually upstream (5') of the coding region of a structural gene, which controls the expression of the coding region by providing recognition and binding sites for RNA polymerase and other factors which may be required for initiation of transcription. The selection of the promoter will depend upon the nucleic acid sequence of interest. In addition to a nucleic acid sequence encoding a protein, any other nucleic acid sequence can be introduced by this method including, for example, regulatory sequences.

Nucleic acid sequences of interest are defined herein as heteropolymers of nucleic acid molecules. The nucleic acid molecules can be double stranded or single stranded and can be a deoxyribonucleotide (DNA) molecule, such as cDNA or genomic DNA, or an ribonucleotide (RNA) molecule. As such, the nucleic acid sequence of interest can, for example, include one or more exons, with or without, as appropriate, introns, as well as one or more of the following optional sequences, in a functional relationship: regulatory sequences (such as promoter sequences), signal or leader sequence, splice donor sites, splice acceptor sites, introns, 5' and 3' untranslated regions, polyadenylation sequences, and negative and/or positive selective markers.

In one example, the nucleic acid molecule contains a single open reading frame which encodes a protein. The nucleic acid of interest is operably linked to a suitable promoter. Optionally, the nucleic acid sequence can be operably linked to a reporter molecule.

The term "operably linked", as used herein, is defined to mean that the nucleotide sequences are linked to a regulatory sequence in a manner which allows expression of the nucleic acid sequence. In general, operably linked means contiguous.

Suitable promoters for use in prokaryotic and eukaryotic cells are well known in the art. Exemplary promoters include the SV4O and human elongation factor (EFI). Other suitable promoters are readily available in the art (see, e.g., Ausubel et al., *Current Protocols in Molecular Biology* (1994–1998) and Sambrook et al., *Molecular Cloning: A Laboratory Manual,* 2nd Ed. (1989)).

Suitable promoters for use in plants are also well known in the art. For example, constitutive promoters for plant gene expression include the octopine synthase, nopaline synthase, or mannopine synthase promoters from Agrobacterium, the cauliflower mosaic virus (35S) promoter, the figwort mosaic virus (FMV) promoter, and the tobacco mosaic virus (TMV) promoter. Specific examples of regulated promoters in plants include the low temperature Kin1 and cor6.6 promoters (Wang, et al., *Plant Mol. Biol.* 28:605 (1995); Wang, et al., *Plant Mol. Biol.* 28:619–634 (1995)), the ABA inducible promoter (Marcotte et al., *Plant Cell* 1:969–976 (1989)), heat shock promoters, and the cold inducible promoter from *B. napus* (White et al., *Plant Physiol.* 106:917 (1994)). Other suitable promoters are readily available in the art.

The term "reporter gene", as used herein, refers to a nucleic acid sequence whose product can be easily assayed, for example, colorimetrically as an enzymatic reaction product, such as the lacZ gene which encodes for β-galactosidase. The reporter gene can be operably linked to a suitable promoter which is optionally linked to a nucleic acid sequence of interest so that expression of the reporter gene can be used to assay integration of the transposon into the genome of a cell and thereby integration of the nucleic acid sequence of interest into the genome of the cell. Examples of widely-used reporter molecules include enzymes such as β-galactosidase, β-glucoronidase, β-glucosidase; luminescent molecules such as green flourescent protein and firefly luciferase; and auxotrophic markers such as His3p and Ura3p. (See, e.g., Chapter 9 in Ausubel, F. M., et al. *Current Protocols in Molecular Biology* , John Wiley & Sons, Inc., (1998)).

The generation of nucleic acid sequences and detection of reporter genes are standard molecular biological procedures well known in the art. Alternative combinations or modifications of the elements according to the present invention would be apparent to the person of skill in the art.

The nucleic acid sequences of interest can be isolated from nature, modified from native sequences or manufactured de novo, as described in, for example, Ausubel et al., *Current Protocols in Molecular Biology,* John Wiley & Sons (1998); and Sambrook et al., *Molecular Cloning: A Laboratory Manual,* 2nd Ed. (1989). The nucleic acids can be isolated and fused together by methods known in the art, such as exploiting and manufacturing compatible cloning or restriction sites.

The term "integrated", as used herein, refers to the insertion of a nucleic acid sequence (e.g., a DNA or RNA sequence) into the genome of a cell or virus as a region which is covalently linked on either side to the native sequences of the cell.

As used herein, a cell refers to a eukaryotic or prokaryotic cell. Typically, the eukaryotic cell is of animal or plant origin and can be a stem cell or somatic cell. The eukaryotic cell can also be a yeast cell, such as, for example, *Saccharomyces cerevisiae*. Suitable animal cells can be of, for example, invertebrate, mammalian or avian origin. Examples of mammalian cells include human (such as HeLa cells), bovine, ovine, porcine, murine (such as embryonic stem cells), rabbit, and monkey (such as COS1 cells) cells. The cell can be a fertilized egg cell, an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions).

Typically, cells isolated from a specific tissue (such as epithelium, fibroblast or hematopoietic cells) are categorized as a cell-type. The cells can be obtained commercially or from a depository or obtained directly from an animal, such as by biopsy. Alternatively, the cell need not be isolated at all from the animal where, for example, it is desirable to deliver the vector to the animal in gene therapy.

The Minos transposable elements can be used to introduce a nucleic acid sequence of interest into the cells of invertebrates. For example, the Minos transposable elements can be used to introduce a DNA sequence of interest into the cells of arthropods. Arthropods include, for example, crustaceans, arachnids, myriapods and insects.

The Minos transposable elements can be used to introduce a nucleic acid sequence of interest into either germ line or somatic cells. The introduction of nucleic acid into germ line cells has the significant advantage that the nucleic acid sequence of interest will be contained in all cells of the mature progeny of the organism and transmitted to its progeny.

The Minos transposable element has been demonstrated to function in a species which is separated from the Minos source species by an evolutionary distance of 600 million years. The Minos transposable element represents the first demonstration of a mobile element which can function autonomously in the germ line of eukaryotes separated by an evolutionary distance of over 100 million years and is likely to lead to the development of a long-sought transformation system applicable across taxonomic barriers (Loukeris et al., *Science* 270:2002–2005 (1995)).

However, even within the dipteran class, significant important applications for the Minos element exist. Listed below are examples of a variety of plant and animal pests, and human disease vectors which fall within the dipteran genus.

| AGRICULTURAL PESTS | COMMON NAME |
|---|---|
| *Ceratitis capitata* | Medfly |
| Anastrepha species | Carribean fruit fly |
| *Bactrocera oleae* | Dacus |
| Bactrocera species | Oriental fruit fly |

| -continued | |
|---|---|
| ANIMAL PESTS | COMMON NAME |
| *Cochliomya hominivorax* | Screw Worm Fly |
| *Lucilia cuprina* | Sheep blowfly |
| Simulium species | Black fly |
| HUMAN DISEASE VECTORS | COMMON NAME |
| Anopheles species | mosquito |
| Aedes species | mosquito |
| *Musca domestica* | house fly |

Methods currently employed to control the populations of certain members of the dipteran class include the release of sterile males. An example of the utility of the germ line transformation methods of this invention includes the improvement of the existing release method. The methods of this invention can be used to improve such methods by enabling sexing schemes and for developing strains with desired characteristics (e.g., improved viability in the field), conditional lethal genes for improved safety, and visible or molecular genetic markers for monitoring. Genetic sexing, i.e. the capability of selectively killing the females (or transforming them into males) in mass-rearing facilities, is recognized as an important need presently. Rearing and releasing only males has several advantages including lower breeding cost and the avoidance of population explosions due to inadvertent release of non-sterilized insects.

For example, the Mediterranean fruit fly (Medfly) *Ceratitis* (*C.*) *capitata* is a major agricultural pest for many fruit species that is geographically widespread in tropical and temperate regions. The Medfly has been introduced relatively recently into the New World, and appears to be spreading rapidly, threatening fruit producing areas in North America (Carey, J. R., *Science* 253: 1369 (1991)). Since the mid 1970's, the sterile insect technique has been used successfully for Medfly eradication and control. This method relies on the decrease in or collapse of fly populations following releases of large numbers of sterile insects over infested areas, and offers an environmentally attractive alternative to massive spraying with insecticides (Knipling, E. F., *Science* 130: 902 (1959)). The germ line transformation methods of this invention can be used to improve the sterile insect technique by, for example, enabling sexing schemes. The germ line transformation methods of this invention can also be used for developing Medfly strains with desired visible markers that can be used for monitoring effective population control.

The methods are also useful for insects for which it might be desirable to introduce new traits in the genetic pool, rather than controlling the population levels. For example, the presence of several sympatric sub-species of *Anopheles gambiae*, all of which transmit malaria, makes it highly unlikely that population control with biological methods such as the sterile insect technique will work. An alternative scheme might involve spreading genes for refractoriness to parasite infection into the existing populations of Anopheles through the use of transposable elements. Population dynamics simulations indicate that this can be effected by releasing relatively small numbers of individuals carrying an autonomously transposing element.

Methods for the introduction of the Minos transposon into germ line cells of diptera are analogous to those previously used in connection with other transposable elements (see, e.g., *Drosophila, A Laboratory Handbook,* Ashburner, M., Cold Spring Harbor Laboratory Press, Cold Spring Harbor, N.Y., (1989)). Briefly, the most common approach is to employ a carrier/helper transposon system. The carrier transposon is a Minos transposon which has been modified by the insertion of a DNA sequence of interest in the region of the transposon flanked by the inverted terminal repeats. Typically, sequences relating to the transposase function are deleted in order to accommodate the nucleic acid of interest. The helper transposon is a Minos transposable element which encodes an active transposase. The transposase catalyzes the transposition of the carrier transposon into the genomic DNA of the germ line of eukaryotic cells. Typically, the helper and carrier are microinjected into the posterior pole of pre-blastoderm embryos, where the precursor cells of the germ line develop.

An alternative to the helper/carrier system involves the purification of active transposase (for example, from an E. coli culture transformed with a recombinant construct encoding the Minos transposase). The purified transposase can be co-introduced into appropriately selected cells along with a carrier transposon to effect integration of the carrier into the recipient genome.

It has now been demonstrated that a nucleic acid sequence of interest can be introduced into a mammalian cell using the Minos transposable elements described herein. Thus, the compositions and methods of the present invention are also useful for the introduction of a nucleic acid sequence of interest into mammalian cells (e.g., mammalian somatic cell, mammalian germ line cell (sperm and egg cells)). This can be accomplished by inserting an isolated transposable element of the type described herein, modified to include the nucleic acid sequence of interest flanked by the termini of the isolated transposable element, into a nucleic acid vector, e.g., a DNA vector, such as a plasmid, virus or other suitable replicon (e.g., a viral vector), which can be present in a single copy or multiple copies. The vector can be introduced into a cell in the presence of a transposase protein or a DNA sequence encoding a transposase protein (e.g., helper plasmid) by a method appropriate to the type of cell (e.g., transformation, transfection). The transposase protein catalyzes the transposition of the modified transposable element containing the nucleic acid of interest into the genomic DNA (chromosome) of the cell. The DNA sequence encoding a transposase protein can also be inserted into a nucleic acid, virus or other suitable replicon and introduced into a cell as described herein. The modified Minos-transposable element and DNA encoding the transposase protein can be incorporated into the same or different vectors. Examples of suitable methods of transfecting or transforming cells include calcium phosphate precipitation, electroporation, microinjection, infection, lipofection and direct uptake. Such methods are described in more detail, for example, in Sambrook et al., *Molecular Cloning: A Laboratory Manual*, Second Edition (1989) and Ausubel, et al., *Current Protocols in Molecular Biology* (1994–1997).

As a particular example of the above approach to introducing the modified transposable element and/or DNA encoding a transposase protein (helper plasmid) into a mammalian cell, the modified transposable element and/or helper plasmid can be integrated into the genome of a virus that enters the cell. The virus is then introduced into the cell in the presence of a transposase protein, or a DNA sequence or virus encoding a transposase protein (helper plasmid). The modified transposable element and helper plasmid can be incorporated into the same or different viral vectors.

Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, *In Fundamental Virology*, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus, lentiviruses and baculoviruses.

A modified transposable element containing the nucleic acid sequence of interest can also be introduced into a cell by targeting the modified transposable element to cell membrane phospholipids. For example, targeting of a modified transposable element of the type described herein can be accomplished by linking the molecule to a VSV-G protein, a viral protein with affinity for all cell membrane phospholipids. Such a construct can be produced using methods well known to those practiced in the art.

A modified transposable element, as described herein, can also be introduced into a cell in a liposome preparation or in another appropriate vehicle. The liposome preparation can be comprised of any liposomes which penetrate the cell surface and fuse with the cell membrane, resulting in delivery of the contents of the liposome into the cell. For example, liposomes such as those described in Yarosh, U.S. Pat. No. 5,077,211; Redziniak et al., U.S. Pat. No. 4,621, 023; and Redziniak et al., U.S. Pat. No. 4,508,703 can be used. The teachings of these patents are incorporated herein by reference.

In a particular embodiment, the Minos transposon-based method can be used to produce transgenic animals. The term "transgenic animal" is a term of art which refers to the introduction of foreign nucleic acid sequences into the germline of an animal by, for example, introduction of the additional foreign genetic material to a gamete such as the egg. As used herein, the term "foreign nucleic acid sequence" refers to genetic material obtained from a source other than the parental germplasm. As used herein, the term "foreign nucleic acid sequence" also includes genetic material obtained from the parental organism itself. Preferably, the transgenic animals are derived from mammalian embryos. The term "mammalian", as defined herein, refers to any vertebrate animal, including monotremes, marsupials and placental, that suckle their young and either give birth to living young (eutharian or placental mammals) or are egg-laying (metatharian or nonplacental mammals). Examples of mammalian species include primates (e.g., monkeys, chimpanzees), rodents (e.g., rats, mice, guinea pigs) and ruminants (e.g., cows, pigs, horses).

Methods for acquiring, culturing, maintaining and introducing foreign nucleic acid sequences into recipient eggs for transgenic animal production are well known in the art. See, for example, *Manipulating the Mouse Embryo: A Laboratory Manual*, Hogan et al., Cold Spring Harbor Laboratory (1986). Preferably, the nucleic acid sequence of interest (e.g., foreign nucleic acid) will be delivered by the Minos-based transposon system into the embryo at a very early stage in development so that only a small frequency of the embryos are mosaic (e.g., an embryo in which integration of the foreign nucleic acid occurs after the one cell stage of development).

A transposon-based method for producing transgenic animals or for stable transfection of cells in vitro has very important advantages compared to the methodology presently used. For example, stable integration of nucleic acids into the germ line of several mammals is now routinely achieved by micro-injecting linear DNA molecules into the nucleus of early embryos. Some of the animals that develop from injected embryos are mosaics for integration events and in only a fraction of these the germ line is involved. Moreover, most events consist of integration of tandem repeats of the injected DNA; single-insertion events do occur at higher frequencies relative to tandem insertions if DNA is injected at lower concentrations, but at a considerable cost in time and expense because the overall transformation frequencies drop.

Using a defined transposon-transposase system can overcome some or all of these problems. First, as in Drosophila, it may not be necessary to have to inject the DNA into the nucleus. A mixture of transposon plus helper plasmids (or transposon plus purified transposase) that is active when introduced into the cytoplasm would enable replacement of costly and time-consuming micro-injection techniques with other methods, such as use of liposomes or viruses. Second, by controlling the relative transposon/transposase levels, the overall efficiency can be improved, with a parallel increase of the frequency of single-insertion events.

The compositions and methods of the present invention are also useful for the introduction of a nucleic acid sequence of interest into a plant cell to produce transgenic plants. As used herein, the term "transgenic plant" refers to the introduction of foreign nucleic acid sequences into the nuclear, mitochondrial or plastid genome of a plant. As used herein, the term "plant" is defined as a unicellular or multicellular organism capable of photosynthesis. This includes the prokaryotic and eukaryotic algae (including cyanophyta and blue-green algae), eukaryotic photosynthetic protists, non-vascular and vascular multicellular photosynthetic organisms, including angiosperms (monocots and dicots), gymnosperms, spore-bearing and vegetatively-reproducing plants. Also included are unicellular and multicellular fungi.

Production of a transgenic plant can be accomplished by modifying an isolated transposable element of the type described herein to include the nucleic acid sequence of interest flanked by the termini of the isolated transposable element. The modified transposable element can be introduced into a plant cell in the presence of a transposase protein or a nucleic acid sequence or a virus encoding a transposase protein (e.g., helper plasmid) using techniques well known in the art. Exemplary techniques are discussed in detail in Gelvin et al., "Plant Molecular Biology Manual", 2nd Ed., Kluwen Academic Publishers, Boston (1995), the teachings of which are incorporated herein by reference. The transposase protein catalyzes the transposition of the modified transposable element containing the nucleic acid sequence of interest into the genomic DNA of the plant.

For example, for grasses such as maize, the elements of the transposon-based method can be introduced into a cell using, for example, microprojectile bombardment (see, e.g., Sanford, J. C., et al., U.S. Pat. No. 5,100,792 (1992). In this approach, the elements of the transposon-based method are coated onto small particles which are then introduced into the targeted tissue (cells) via high velocity ballistic penetration. The transformed cells are then cultivated under conditions appropriate for the regeneration of plants, resulting in production of transgenic plants. Transgenic plants carrying a nucleic acid sequence of interest are examined for the desired phenotype using a variety of methods including, but not limited to, an appropriate phenotypic marker, such as antibiotic resistance or herbicide resistance, or visual observation of the time of floral induction compared to naturally-occurring plants.

A modified transposable element, as described herein, can also be introduced into a plant cell by Agrobacterium-mediated transformation (see, e.g., Smith, R. H., et al., U.S. Pat. No. 5,164,310 (1992)) or electroporation (see, e.g., Calvin, N., U.S. Pat. No. 5,098,843 (1992)), or by using laser beams (see, e.g., Kasuya, T., et al., U.S. Pat. No. 5,013,660 (1991)) or agents such as polyethylene glycol (see, e.g., Golds, T. et al., *Biotechnology,* 11:95–97 (1993)), and the like. A modified transposable element, as described herein, can also be inserted into a nucleic acid vector (e.g. an episomal vector or a Ti plasmid vector), or virus or other suitable replicon (e.g., a viral vector), which can be present in a single copy or multiple copies. Viral vectors which can be introduced into plant cells include cauliflower mosaic virus, figwort mosaic virus, and tobacco mosaic virus.

The vector can be introduced into a plant cell in the presence of a transposase protein, a nucleic acid sequence encoding a transposase protein (e.g., helper plasmid) or a virus encoding a nucleic acid sequence encoding a transposase protein using techniques well known in the art. The method of introduction of the elements of the transposon based system into the plant cell is not critical to this invention.

The present invention also provides vectors containing an isolated Minos transposable element and nucleic acid sequence of interest. Suitable vectors for use in eukaryotic and procaryote cells are well known in the art and are, generally commercially available, or readily prepared by the skilled artisan. For example, suitable plasmids for use include pUC119 and pBlueScript KS. Additional vectors can also be found in, for example, Ausubel et al., *Current Protocols in Molecular Biology,* John Wiley & Sons (1998); Sambrook et al., *Molecular Cloning: A Laboratory Manual,* 2nd Ed. (1989); and Gelvin et al., supra (1995), the teachings of which are incorporated herein by reference.

The novel Minos-based stable transfection system of the present invention can be particularly useful in the delivery of one or more nucleic acid sequences of interest (e.g., genes) or products thereof to a patient. Generally, the nucleic acid sequence of interest is present or has been incorporated into the genome of the viral vector. The nucleic acid sequence or the product thereof can be a therapeutic agent. An example of a therapeutic nucleic acid sequence include RNA (e.g., ribozymes) and antisense DNA that prevents or interferes with the expression of an undesired protein in the target cell. The nucleic acid sequence of interest can also encode a heterologous therapeutic protein. A heterologous protein or nucleic acid sequence is one which does not exist in the virus as it is found in nature. Examples of therapeutic proteins include antigens or immunogens such as a polyvalent vaccine, cytokines, tumor necrosis factor, interferons, interleukins, adenosine deaminase, insulin, T-cell receptors, soluble CD4, epidermal growth factor, human growth factor, blood factors, such as Factor VIII, Factor IX, cytochrome b, glucocerebrosidase, ApoE, ApoC, ApoAI, the LDL receptor, negative selection markers or "suicide proteins", such as thymidine kinase (including the HSV, CMV, VZV TK), anti-angiogenic factors, Fc receptors, plasminogen activators, such as t-PA, u-PA and streptokinase, dopamine, MHC, tumor suppressor genes such as p53 and Rb, monoclonal antibodies or antigen binding fragments thereof, drug resistance genes, ion channels, such as a calcium channel or a potassium channel, and adrenergic receptors.

The invention can be particularly useful for vaccine delivery. In this aspect of the invention, the antigen or immunogen can be expressed heterologously (e.g., by recombinant insertion of a nucleic acid sequence which encodes the antigen) or immunogen (including antigenic or immunogenic fragments) in a viral vector. Alternatively, the antigen or immunogen can be expressed in a live attenuated, pseudotyped virus vaccine, for example. Generally, the methods can be used to generate humoral and cellular immune responses, e.g. via expression of heterologous pathogen-derived proteins or fragments thereof in specific target cells.

Generally, viral vectors which contain therapeutic nucleic acid sequences of interest are known in the art. Examples include the vectors described in Anderson, et al. (U.S. Pat. No. 5,399,346), Sambrook, et al., supra, Ausubel, et al., supra, and Weiss, et al. (1985) *RNA Tumor Viruses,* Cold Spring Harbor, N.Y., the contents of which are incorporated herein by reference.

Also envisioned are the use of these viral vectors comprising a modified Minos transposable element and the transposase or nucleic acid sequence encoding the transposase protein for in vivo and ex vivo gene therapy.

Where a target cell is contacted in vitro, the target cell incorporating the viral vector comprising a Minos transposable element modified to include a nucleic acid of interest and the transposase or nucleic acid sequence encoding the transposase protein can be implanted into a patient for delivery of the nucleic acid of interest or product thereof. The "nucleic acid of interest" is meant to refer to a gene or RNA encoded by a gene for which the patient has an insufficiency or deficiency. The "target cell" as used herein can be migratory, such as a hematopoietic cell, or non-migratory, such as a solid tumor cell or fibroblast. Frequently, the target cell is present in a biological sample obtained from the patient (e.g., blood, bone marrow). After treatment (contact with the viral vector comprising the modified Minos transposable element and transposase protein or nucleic acid sequence encoding the transposase protein), the sample is returned or readministered to (reintroduced into) the individual according to methods known to those practiced in the art. Such a treating procedure is sometimes referred to as ex vivo treatment. Ex vivo gene therapy has been described, for example, in Kasid et al., *Proc. Natl. Acad. Sci. USA,* 87:473 (1990); Rosenberg et al., *N. Engl. J. Med.,* 323:570 (1990); Williams et al., *Nature,* 310:476 (1984); Dick et al., *Cell,* 42:71 (1985); Keller et al., *Nature,* 318:149 (1985); and Anderson, et al., U.S. Pat. No. 5,399,346.

The modified transposable element and helper plasmid can be incorporated into the same or separate viral vectors. Where the modified transposable element and helper plasmid are incorporated into separate viral vectors, the viral vector comprising the modified transposable element and the viral vector comprising the helper plasmid can be simultaneously or sequentially introduced into a cell. The viral vector comprising the modified Minos-transposon can be introduced into a cell prior to the viral vector comprising the helper plasmid. Alternatively, the viral vector comprising the helper plasmid can be introduced into the cell prior to the viral vector comprising the modified Minos-transposon.

The mode of administration to a patient is preferably at the location of the target cells. As such, the administration can be nasally (as in administering a vector expressing ADA) orally (as in an inhalant or spray as in administering a vector expressing the cystic fibrosis transmembrane conductance regulator (CFTR)) or by injection (as in administering a vector expressing a suicide gene to a tumor). Other modes of administration (e.g., parenteral, mucosal, systemic, implant or intraperitoneal) are generally known in the art. The agents can, preferably, be administered in a pharmaceutically acceptable carrier, such as saline, sterile water, Ringer's solution, and isotonic sodium chloride solution.

Also encompassed by the present invention is the use of the Minos transposable elements and Minos transposase to induce mutations in a cell and to identify mutations of interest in a cell. Further encompassed by the present invention is the use of the Minos transposon elements and Minos transposase to identify genes containing mutations of interest in a cell.

As used herein, the term "mutation" refers to a change or disruption in a gene which leads to a phenotype (e.g., physical, biochemical, clinical, molecular, enzymatic, immunological or pharmacological) different from that of the nonmutated cell or animal. For example, a mutation in a cell which is normally round in appearance can result in a spindle shaped cell. Similarly, a mutation in a cell which normally metabolizes a substrate can lead to an inability to metabolize the substrate. A mutation can be silent. As used herein, a silent mutation includes changes which occur in the genetic material of a cell or animal but is not distinguished from the nonmutant cell or animal on the basis of phenotype.

A gene responsible for a mutation of interest can be identified by introducing a Minos transposon, modified to include an indicator (e.g., a reporter or selectable marker gene) flanked by the termini of the isolated transposon, into a collection of cells in the presence of a transposase protein or a nucleic acid sequence encoding a transposase protein under conditions suitable for integration into the genome of a cell using techniques well known in the art. The term "indicator", as used herein, refers to a means to determine whether the transposon has integrated into the genetic material (e.g., chromosome) of a cell. For example, an indicator includes a reporter (e.g., lac Z) or selectable marker (e.g., neomycin) gene product. In a particular embodiment, the modified transposon and transposase are transfected into the collection of cells using viral vector mediated transfection schemes. Following transfection, integration can be detected. For example, in a particular embodiment, reporter gene expression can be induced under appropriate conditions and cells which have integrated into their genome the Minos transposon can be identified. Experimental conditions for the detection of reporter genes are well known in the art.

Integration of the Minos transposon can induce a mutation of interest in the genome of a cell. A cell in which the mutation of interest is present is identified by a change in phenotype and clonally propagated using standard techniques well known in the art. The phenotypic change will depend on the cell type and will be readily apparent to one of skill in the art. The gene of interest is then identified, cloned and analyzed by the presence of the Minos transposon sequence using standard molecular hybridization techniques, such as in situ hybridization, Southern blotting, and colony hybridization, employing the sequence (e.g., the entire sequence or a fragment thereof) of the Minos transposon element as a probe using art-recognized methods. (See, e.g., Ausubel et al., *Current Protocols in Molecular Biology,* John Wiley & Sons (1998); and Sambrook et al., *Molecular Cloning: A Laboratory Manual,* 2nd Ed. (1989)).

A unique advantage of the transposon system described herein compared to other mutagenesis systems is the potential to be able to reverse the mutation of interest in a cell by introduction of the transposase protein or a nucleic acid sequence encoding the transposase protein. Therefore, after cloning of cells with a mutation of interest and cloning of the gene responsible for the mutation of interest, some of the clonal cells containing the mutation of interest can be subsequently used to confirm that a particular mutant phenotype is the result of integration of the modified Minos transposon. This is accomplished by the introduction into the cells of a Minos transposase protein, or a nucleic acid sequence or virus encoding a Minos transposase protein. The transposase catalyzes a site-specific excision of the transposon dictated by the inverted terminal repeats at the 5' and 3' ends of the transposon leaving behind a characteristic six base pair segment consisting of the four terminal nucleotides of either side of the transposon and the TA target site at the location of integration in the genome of the cell (Arcà, B. et al., *Genetics* 145:267–279 (1997)). The transposase excises the Minos transposon while repairing and rejoining the chromatin thereby reversing the mutation in many cases (e.g., mutant phenotype to wildtype phenotype).

The random integration of the Minos-transposon can be mutagenic in a cell in vitro as discussed above. As a result, the Minos-transposon and transposase can be used to induce mutations in a cell or animal. The Minos-transposon and transposase can also be used, for example, in in vivo or in vitro to induce reversion of a Minos-induced mutation, as described herein. It is envisioned that the methods and compositions of the present invention can be used to induce random excision (removal) events in the genome of somatic cells during development of an animal or differentiation of a cell, thereby permitting the generation of mutations during development of an animal or differentiation of a cell. The developmental consequences of the mutations can then be evaluated. Differentiation refers to acquisition or possession of characteristics or functions differing from that of the original type. For example, a differentiated erythroblast cell is an erythrocyte.

Using the Minos-transposon and transposase of the invention, a recombination system can be employed to delete a gene segment with precision in a cell (e.g., embryonic stem cell). In a particular embodiment, an isolated Minos transposable element, modified to include a nucleic acid sequence of interest (e.g., an indicator gene) flanked by the inverted terminal repeats of the isolated transposable element is introduced into a cell. The transposon can be introduced either by the transposase-dependent methodology of the invention or by conventional transgenesis or by other means such as another transposable element. The transposon and a transposase protein, or nucleic acid modified Minos transposable element and the transposase or nucleic acid sequence encoding the transposase protein sequence or virus encoding a transposase protein are then introduced into the cell. To facilitate identification and selection of cells harboring the integrated transposon and nucleic acid sequence of interest from cells having undergone Minos transposase-mediated DNA recombination (e.g., excision), tandemly linked bacterial neomycin resistance (neo) and herpes simplex virus thymidine kinase (HSV-tk) genes are included in the modified Minos transposon vector. The neo and HSV-tk sites will serve as positive and negative selection markers, respectively. Other suitable selection markers are known in the art and can also be used. Selected cells are clonally propagated. Selection and cloning processes are techniques well known and readily available in the art.

Thus, the Minos-transposon and transposase system can be a valuable tool to mediate recombination and reverse and induce mutations in cells and transgenic animals. This method can be efficient for the introduction of deletions of defined regions and lengths in the genome of a cell.

To generate a transposon induced mutation in a gene of interest in a cell, an isolated Minos transposon modified to include an indicator is integrated into the cloned DNA sequence of the gene of interest in such a way that expression of the gene of interest is disrupted. The term "gene of interest" is used to refer to a stretch of DNA in a cell which carries the genetic information for a mRNA molecule and corresponding protein. For example, a gene of interest can be the epidermal growth factor, prolactin, P-selectin or estrogen receptor gene. "Cloned" is a term of art which refers to nucleic acid sequences manufactured by molecular biological techniques.

The introduction of the transposon into the cloned gene of interest can be achieved by conventional recombinant DNA technologies or by the transposase-induced transposition of the transposon, in vivo or in vitro, into a suitable plasmid containing the gene of interest. The plasmid is amplified and used in standard gene targeting protocols to replace the endogenous gene of interest in a cell by homologous recombination/gene conversion techniques. Endogenous means native to the cell and not derived from the cloned DNA. Homologous recombination occurs between the cloned DNA of the gene of interest and the endogenous DNA of the gene of interest thereby targeting the cloned gene of interest into the chromosome. The cells containing the targeted mutation are identified and clonally propagated using well known, routine methodologies described in detail in several art-recognized protocol texts including, for example, Ausubel et al., supra (1998). The cells containing the targeted mutation can be evaluated experimentally. To induce reversion of the targeted mutation in a cell a transposase protein or a nucleic acid encoding the transposase protein, is introduced into a cell(s) resulting in excision of the transposon and in many instances reversion of the mutation. Mutations that can be reversed are those in which the six-base pair footprint remaining after Minos transposon excision does not disrupt expression of the gene.

In a preferred embodiment the cells are embryonic stem cells. The embryonic stem cells are used for gene targeting and the resulting mutant cells are used to create transgenic animals and animals carrying null or "knock-out" mutations. A "knock-out" mutation refers to the disruption of a gene of interest with a complete loss of function. The embryonic stem cells which contain the gene of interest integrated into their genome by the Minos-transposon system can be transmitted to the germline of an animal, such as a mouse, by injection into an early cleavage stage embryo (e.g., blastocyst) or by aggregation with two morulae to produce a chimera. "Chimera" is a term of art intended to mean an embryo containing cells or tissues with two or more genotypes. Chimeras carrying the mutated or foreign nucleic acid sequence in their germ cells are then bred to produce transgenic offspring that are entirely derived from the embryonic stem cells which carry the mutation. Genetic markers such as coat color in mice can be used to distinguished chimeras and animals derived entirely from embryonic stem cells. Experimental techniques for obtaining, propagating, cloning and injecting embryonic stem cells are well known in the art. See, for example, Evans et al., *Nature* 292:154–156 (1981); Rossant et al., *Experimental Approaches to Embryonic Mammalian Development*, Cambridge University Press (1986); Sedivy et al., *Gene Targeting*, W. H. Freeman and Co., New York, N.Y. (1992); Ausubel et al., supra (1998).

The Minos-transposon approach has several advantages over the recombination techniques currently in use such as the Cre/LoxP system. For example, the introduction of nucleic acids sequences of interest is performed directly by the Minos transposon. No additional components, such as target sites, are required. In addition, using the present method, a single copy of a nucleic acid sequence of interest can be integrated and precisely excised from the genetic material of a cell in each integration step.

The invention also relates to the use of the Minos transposable element to identify gene enhancer elements. The term "enhancer", as used herein, refers to any cis-acting nucleic acid sequence that increases or augments the utilization of a gene promoter and can function either upstream or downstream from the promoter. An enhancer element can be close to or distant from the promoter. In this aspect of the invention, an isolated Minos transposable element is modified to include an indicator gene (e.g., nucleic acid sequence encoding a suitable reporter molecule such as β-galactosidase or a selectable marker (e.g., neomycin resistance) flanked by the inverted repeats of the isolated transposable element, which is optionally linked to a minimal promoter (e.g., a TATA box sequence). As used herein, the term "minimal promoter" includes nucleotide sequences upstream from the Minos transposon that can weakly initiate transcription.

For enhancer detection methods, the nucleic acid sequence comprising a minimal promoter and Minos transposable element, modified to include an indicator gene (e.g., a reporter gene such as lacZ) or selectable marker such as neomycin gene), is incorporated into a suitable vector, as described herein, and introduced into a population (or sample) of cells under conditions appropriate for integration into the genome of a cell in the presence of a transposase protein or a nucleic acid sequence or virus encoding a transposase protein. Integration into the genome of a cell at or near an enhancer site can be detected by the indicator. For example, selection of cells or detection of the reporter gene product. It is expected that varying ranges of signal, in the case of a reporter gene, and selection, in the case of a selectable marker, can occur depending upon the strength of the enhancer. Once an enhancer region has been identified by, for example, expression of a reporter gene, the enhancer site can be located within the genome by standard hybridization protocols (e.g., in situ hybridization and Southern blotting with Minos transposon specific probes) and the resulting sites readily cloned and analyzed. Experimental conditions for the detection of reporter and selectable marker genes as well as hybridization techniques and genomic sequencing are well known in the art.

The methods and compositions of the present invention can also be used to detect and trap an exon of a gene in a cell. The term "exon", as used herein, is any segment or region of a gene which is represented in the mature mRNA transcription product. Most eukaryotic genes and some prokaryotic genes include additional nucleic sequences referred to as introns that are within the coding region of a gene but do not appear in the mature mRNA. Introns are dispersed among the exons in the genetic material of cells. To identify an exon of interest in a gene, an isolated Minos transposable element is modified to include an indicator gene (e.g., reporter or selectable marker gene) lacking a translation initiation codon but linked to a splice acceptor sequence and flanked by the inverted terminal repeats of the isolated transposable element. The modified transposable element is incorporated into an appropriate vector and introduced into a population of cells in the presence of a transposase protein or a nucleic acid sequence encoding a transposase protein. In a particular embodiment, the modified transposable element and/or the transposase is incorporated into a viral vector, which is introduced into a population of cells. Random integration of the transposon into an intron of a gene in the correct orientation can result in transcription of hybrid mRNA encoding, for example, an indicator gene, such as a reporter or marker gene. mRNA transcribed from a gene disrupted by integration of the modified transposon in an intron results in a change in mRNA splicing patterns compared to the gene lacking the integrated transposon in such a way that a hybrid mRNA is produced carrying, for example, the reporter or marker gene as an exon. This change in splicing pattern signifies the presence of an exon. Genes targeted in this way can be isolated by virtue of their being linked to the Minos transposon. Methods for transfection, reporter gene expression, selection conditions, mRNA isolation, reverse transcription protocols, nucleic acid sequencing and hybridization techniques are all well known art-recognized technologies. Exemplary discussions and detailed protocols can be found in Ausubel et al., supra and Sambrook et al., supra.

The gene- and enhancer-trapping strategies described above can provide for a novel and relatively simple method of identifying developmentally regulated genes. For example, reporter genes lacking promoters can be randomly integrated into the genome of a cell by using the Minos-based transposon system described herein. For example, a modified transposon element containing a "promoter-less" reporter gene can be introduced into mouse embryonic stem cells, which are then introduced into embryos. Screening for expression of the reporter gene permits the identification of endogenous genes which become transcriptionally active in the developing embryo or in the embryonic stem cells in vitro. The molecular tag provided by the Minos transposon enables developmentally expressed and regulated genes to be readily identified, cloned and analyzed.

METHODS FOR ISOLATING ADDITIONAL Tc-1 FAMILY MEMBERS

DNA sequence analysis of the members of the Minos family disclosed herein, and comparison of this sequence information to the sequences of Tc-1 family members from evolutionarily distant organisms (e.g., nematode), reveal short stretches of conserved amino acid sequence within the transposase coding region. This high degree of conservation suggests a method for isolating Tc-1 family members from diverse eukaryotic species.

This method involves the amplification of DNA by polymerase chain reaction from a eukaryote of interest using primers which are complementary to a sequence of at least about 12 consecutive nucleotides which encode amino acids which are highly conserved in aligned sequences of nematode Tc-1 family members and dipteran Minos family members. Such amino acid sequences include, for example, MVWGC (SEQ ID NO:10), WPSQSPDL (SEQ ID NO:11) and WPSNSPDL (SEQ ID NO:12).

The present invention will now be illustrated by the following examples, which are not intended to be limiting in any way.

EXAMPLES

Example 1

Materials and Methods

1. Fly Strains

Standard procedures were used for culturing of *Drosophila hydei*. All strains used in this study have been used previously for rDNA work and are named for the X and Y chromosomes. Strain bb[1] (bb[1]/bb[1]×bb[1]/Y) carries a bobbed X chromosome; strain X[7] (X[7]/X[7]×X[7]/Y) is a subline of the Dusseldorf wild-type strain; strain X^X/Y(X^X/Y×X/Y) females carry a compound X chromosome which has no rDNA. Strain wm1/Y (wm1/Y×X–3/Y) females have a compound X chromosome (wm1); males carry a X-autosome 3 translocation which has no rDNA.

2. DNA Manipulating and Sequencing

All basic procedures were carried out essentially as described (Maniatis et al., 1982). DNA from adult females of strain bb[1] was partially digested with EcoRI and cloned into phage vector λgt7. To recover new Minos elements, the library was screened by hybridization with a 1.7 kb HhaI fragment which contains most of the Minos-1 sequence. For sequencing, the appropriate restriction fragments from positive clones were subcloned into plasmid vectors pUC8 and pUC9 and nested deletions were generated by digestion with exonuclease Bal31 followed by subcloning. Sequencing was performed by conventional methods. Both strands were sequenced, with a minimum of two independent sequences for each base pair.

3. Sequence Analysis

Database searches and sequence analysis and manipulations were performed using programs FASTA (Pearson and Lipman, *Proc. Natl. Acad. Sci. USA* 85:2444–2448 (1988)). BLAST (Altschul et al., *J. Mol. Biol.* 215:403–410 (1990)) and the computer package GCG (Devereux et al., *Nuc. Acids Res.* 12:387–395 (1984)). The program CLUSTAL (Higgins and Sharp, 1988) was used for protein sequence alignments.

Results

1. The Sequence of Minos

Three new representatives of the Minos family of transposable elements have been cloned and sequenced; they have been named Minos-2, Minos-3 and Minos-4, Minos-1 being the element reported previously. Minos-2 and Minos-3 are complete elements distinct from Minos-1, as judged from the restriction maps of the flanking DNA and the flanking sequences. The sequences of the elements, summarized in FIGS. 2A–2C, show very little variation, differing in only two positions. At position 900 of the sequence, Minos-2 and Minos-3 have a G instead of the A found in Minos-1. This transition changes a TAG stop codon to TGG and restores a 603 bp ORF beginning with ATG at position 878. The second difference is at nucleotide 1161, which is a C in Minos-1 and Minos-3 and a T in Minos-2. This causes a ser→leu substitution in ORF2 of Minos-2, relative to Minos-1 and Minos-3. Minos-2 and Minos-3, therefore, have two complete ORFs beginning with an ATG; ORF1, which can encode a 133 amino-acid peptide, and ORF2, which can encode a 201 amino-acid peptide.

The Minos-4 clone does not contain a complete element. The sequence of the cloned DNA fragment begins at the EcoRI site found at position 1172 of the other members and is identical to the Minos-1 sequence to base 1779. Apparently Minos-4 represents a partial isolate rather than a defective member of the family, since the library from which it was isolated was from DNA cut with EcoRI.

The DNA sequence flanking the cloned elements are different from each other; this indicates that these elements are inserted at different sites of the *D. hydei* genome, and are, therefore, distinct. These sequences are mainly characterized by a high A/T content, and do not show any other obvious similarity. In all cases, the inverted repeats end with the dinucleotide TA, which is at the same time a direct and an inverted repeat. Because of this, there is some ambiguity in defining the ends of the element precisely. Shown below are the sequences of the Minos 1–4 insertions sites. The rDNA sequences flanking the Minos elements are shown in lower case and Minos sequences are shown in upper case. The rDNA sequence identical to the flanking DNA of Minos-1 has been aligned with the Minos-1 insertion sequence. It is noted that since gapped sequences are treated as separate sequences for purposes of the Rules of Practice in Patent Cases (37 CFR 1.822(o)), and since each of the separate sequences contain less than 10 nucleotides, the sequences shown below have not been listed in the Sequence Listing.

In the case of Minos-1, which is inserted into a region which has been previously sequenced, the external transcribed spacer of the rDNA repeat, there are two possibilities. As shown below, deleting the sequence which begins with ACGA and end with TCGT would restore the rDNA sequence; the element, with an A and a T at the two ends may have inserted between a T and an A. In this possibility, the element would be 1779 bp long with 255 bp inverted repeats. Alternatively, the element may begin and end with CGA . . . TCG and produce a target site duplication, as happens with many other mobile elements. In this possibility the target site duplication would involve the dinucleotide TA, and the size of the element would be 1777 bp. For numbering, the A of the TA repeat has been designated nucleotide number 1 of the Minos-1–3 sequences.

```
rDNA        ataat-------------------attaa

Minos-1     ataatACGA------------TCGTattaa

Minos-2     aatatACGA------------TCGTataat

Minos-3     gctttACGA------------TCGTagaag

Minos-4     tttctACGA                    |
                      |
                   1775              1
```

2. Mobility and Homogeneity of Minos Elements

The striking degree of sequence conservation among the cloned Minos elements suggests that, as in the case of Tc1, all Minos elements may be highly homogeneous. To test this the single HhaI site within each of the terminal repeats of Minos was exploited. The 1.68 kB HhaI fragment of Minos-1 was used as probe in a Southern blot of genomic DNA from the same strains, digested with CfoI, an isoschisomer of HhaI. A single, strong band of approximately 1.7 kb was detectable in all lanes, indicating that no major deletions or rearrangements are present in the Minos elements present in these strains.

3. Comparison of the Protiens Encoded by Tc1 and Minos

The deduced 201 amino acid sequence of the ORF2 in Minos-2 and Minos-3 shows significant sequence similarity with the 201 carboxy terminal residues of TcA, the putative transposase of Tc1; alignment of the sequences gives 63 identities (31%) and 91 conservative substitutions (45%) with only two single-residue insertion-deletions. The two sequences, however, differ in size; TcA has 72 additional amino acids at the amino end. The 50 amino-terminal residues of TcA show weak but significant sequence similarity with the carboxy terminus of Minos ORF2; introduction of a 60-bp deletion in the Minos DNA sequence creates a long open reading frame which contains most of ORF1 (codons 1 to 138) and the entire ORF2 extended by 22 codons upstream of the ATG. Interestingly, this 60-bp sequence, from base 752 to base 811 of the Minos sequence, exhibits features of an intron. More specifically, the 5' and 3' ends conform to the consensus splice donor and acceptor sites and a version of the internal splice signal consensus is found 30 nucleotides upstream from the 3' end.

4. Divergence of the TcA-Related Sequences

Although Minos inhabits a Drosophila species, it is not more related to the other Tc1-like elements from Drosophila species, HB1 and Uhu. These elements, or at least the members which have been sequenced, do not contain open reading frames comparable in length to that of Tc1. However, if small numbers of deletions and insertions are introduced in their DNA sequences, open reading frames can be generated which show significantly similarity with the TcA sequence. Most of these insertion-deletion changes involve one nucleotide, presumably representing mutations which have accumulated in these inactive elements. Table 1 shows a similarity matrix between the three Drosophila and the two nematode elements, in the regions corresponding to the hypothetical Minos exon 2. In Table 1, percent identities are shown above the diagonal; identical/total positions are shown below the diagonal. Minos shows approximately the same degree of similarity (between 28 and 36 percent identity) with all the other elements; HB1 and Uhu show comparable similarities. In a multiple sequence alignment of the same regions, 21 of the resulting 225 positions (9%) are invariant and 49 positions (22%) are occupied by related amino acids. It should also be noted that the similarity between HB1 and Uhu with Tc1 and Minos extends another 18 codons upstream from the position corresponding to the first codon of the hypothetical exon 2 of Minos. No other significant similarities can be detected between Tc1, Uhu, HB1 and Minos in the sequences between the terminal repeats.

TABLE 1

|       | Tc1     | TCb1    | Minos   | Uhu    | HB1 |
|-------|---------|---------|---------|--------|-----|
| Tc1   |         | 71      | 31      | 44     | 33  |
| TCb1  | 160/223 |         | 34      | 41     | 35  |
| Minos | 70/221  | 75/222  |         | 36     | 28  |
| Uhu   | 96/217  | 89/217  | 78/218  |        | 31  |
| HB1   | 73/223  | 79/223  | 62/222  | 68/219 |     |

5. The ORF1 Sequence is Related to the Paired Box Sequence

Searches of the nucleic acid and protein sequence data libraries with the ORF1 sequence using the FASTA and WORDSEARCH algorithms gave no significant matches. However, the Basic Local Alignment Search Tool program revealed a similarity with the paired box sequence, a peptide sequence found in the Drosophila paired gene product, and conserved in other Drosophila and mammalian genes. This similarity extends approximately between residues 1 to 96 of the Minos sequence, and residues 35 to 131 of the Drosophila paired protein. Alignment of the Minos sequence with the Drosophila and human paired box sequences for maximum similarity shows 16 invariant positions in this region (17%) and 49 positions occupied by related amino acids (51t). The corresponding values for the human and Drosophila paired sequences are 72% identities and 23% conserved positions.

Although the Minos-paired similarity is weak compared to that between the Drosophila and human paired sequences, it is statistically significant. The similarity scores between the Minos sequence (amino acids 1 to 118 of ORF1) to the corresponding human paired sequence (amino acids 17 to 135 of the published sequence) is approximately 10 standard deviations higher than the average of the scores obtained from 50 comparisons made between the Minos sequence and 50 randomly shuffled human paired sequences.

6. Transposition in D. melanogaster

A D. melanogaster "helper" strain which can overproduce the Minos transposase upon exposure to heat shock was constructed. The strain was constructed by introducing a modified Minos element into the germ line by conventional P element transformation (see, e.g., Drosophila, "A Laboratory Handbook", Ashburner, M., Cold Spring Harbor Laboratory Press, Cold Spring Harbor, N.Y., (1989)). To place the Minos transposase under heat shock control, the left-hand terminal repeat of Minos-2 was replaced by the D. melanogaster hsp 70 promoter. This modified element was inserted into the P element transformation vector pDM30, which contains a wild-type copy of the Drosophila rosy (ry) gene as a dominant visible marker. The plasmid (pPhsM2) was injected into pre-blastoderm embryos of a ry strain, injected G0 adults were mated to ry flies and $ry^+$ G1 progeny were bred further. Three independent transformants were recovered, two on the third chromosome (named M46 and M67) and one on the X (M84). Southern blots using ry and Minos probes indicated that each of the three transformants contains a single insertion of the complete sequence between the P element ends. Northern blots of total RNA from adult transformed flies subjected to a heat shock showed abundant transcripts hybridizing to Minos probes. No Minos-related transcripts have been detected by the same probes in RNA from non-heat shocked flies. The structure of the RNA transcripts was investigated in another series of experiments discussed below.

Breeding of these transformants showed that they are all homozygous lethal. This observation was unexpected; the recovery of recessive lethal mutations due to insertional inactivation of essential genes is a rather uncommon event in P transformation experiments. Moreover, the insertion into the X clearly has not caused a "knock-out" mutation since hemizygous males are viable and fertile; only homozygous females are inviable. This behavior suggested that the lethality may be dosage- or pairing-dependent; the latter being more likely because double heterozygotes of the two insertions in the 3rd chromosome are viable. The observed lethality is a useful feature which enables one to follow the segregation of the "helper" chromosomes by keeping them over genetically marked balancers.

Strong evidence for Minos transposition in the germ line was obtained by first introducing the M67 chromosome into a white background (y,w; TM3/M67). Pre-blastoderm embryos were injected with a plasmid (pM2w) containing a complete Minos-2 element with a wild-type copy of the white (w) gene inserted into its unique EcoRI restriction site within ORF2. The inserted w sequences provide a dominant selectable marker; in addition they interrupt ORF2, making the production of active transposase from this construct highly improbable. Three separate experiments were conducted: In experiment A injected embryos and the developing larvae and adults were kept at 18 degrees C., in experiment B they were kept at 25 degrees C. throughout development, and in experiment C the embryos were subjected to a 1-hour 37° C. heat shock three hours after injection. All emerging G0 flies (63, 38 and 61, from experiments A, B and C, respectively) were mated to y,w; TM3/Dgl3 flies and the progeny were scored for the appearance of the w⁺ phenotype. To date, at least four independent germ line transformation events have been detected in experiments A and B. Two of these events come from a single G0 male from experiment A and at least two have been recovered from two different G0 flies from experiment B. The results are shown in Table 2 below:

TABLE 2

| Experiment | G0 | #G1 Scored | w⁺ G1 | Insertion Chromasome |
|---|---|---|---|---|
| A | A10 | 286 | A10.1 | X |
|   |     |     | A10.2 | 3 |
|   |     |     | A10.3 | 3 |
|   |     |     | A10.4 |   |
|   |     |     | A10.5 |   |
|   |     |     | A10.6 | ? |
| B | B13 | 75  | B13.1–3 | ? |
| C | B33 | 116 | B33.1–18 | ? |

Evidence that the Minos-w⁺ transposon can be mobilized in the soma of flies which produce the transposase has been obtained. Larvae of the constitution y,w; TM3/[M2w]M67 (progeny of the A10.2 fly), which contain both transposon and helper sequences, were subjected to heat shock and adult flies were examined for the appearance of eye color mosaicism. More than 50% of the flies showed mosaicism of different degrees. Patches of ommatidia with either reduced or increased pigmentation were observed which is consistent with the expected result of a somatic deletion or transposition event. No mosaicism has been detected in flies not subjected to a heat shock at the larval stage. The somatic instability results clearly indicate that the w⁺ insertions are minos-mediated.

7. Analysis of Minos mRNA Transcripts

Total RNA was isolated from the M67 strain, the construction of which is described above. The structure of mRNA transcripts was investigated by the polymerase chain reaction (PCR) method of DNA amplification. A particularly important aspect of this investigation was to determine the status of the 60 base pair putative intron region (discussed above) in the mRNA transcripts. As was mentioned previously, this sequence is characterized by 5' and 3' ends which conform to the consensus splice donor and acceptor sites, and has a version of the internal splice signal consensus sequence 30 nucleotides upstream from the 3' end.

To determine the status of this putative intron, PCR priming sites were selected from exon sequences (ORF1 and ORF2) flanking the putative intron. The PCR product synthesized in this reaction was cloned and sequenced by conventional methods. The sequencing experiments revealed unambiguously that the 60 base pair intron sequence was, in fact, absent in the amplified DNA.

The removal of the 60-bp sequence in the correctly spliced primary transcript initiating upstream from ORF1, results in the generation of a 1023-bp open reading frame which encodes a peptide of 341 amino acids. An alignment of the 273 carboxy-terminal amino acids of this peptide with the sequences of TcA and the 273-residue hypothetical peptide of TCb1 was generated by the multiple alignment program CLUSTAL, which introduces gaps in the sequences to achieve maximum sequence similarity. The three sequences were aligned without the need of any insertions-deletions (with the exception of the two one-residue gaps required for optimal alignment in the ORF2 region) and show an overall 28% identity, i.e. 76 of the 273 positions are invariant. In the region upstream from the first methionine of ORF2, twelve out of seventy two positions (16%) are invariant; 29 positions (40%) are occupied by structurally related amino acid residues. Although this degree of similarity is lower than that in the ORF2 region, it is statistically significant.

The sequence similarity between TcA and the carboxy end of the Minos hypothetical protein is also reflected in their secondary structures. Comparisons of α-helix and β-sheet predictions and hydrophobicity profiles between the Tc1 and Minos sequence show similarities in several regions. Another feature of the sequences is their high content, approximately 20%, in basic amino acids. TcA has 29 arginines, 16 lysines and 11 histidines, and the TcA-related Minos sequence has 20 arginines, 32 lysines and 4 histidines. These are more abundant at the amino-terminal half of both sequences, although the position of most is not strictly conserved. The proteins are fairly basic, with computed isoelectric points of 11.27 for TcA and 10.73 for the related Minos peptide. The computed pI of the complete hypothetical 361 amino acid Minos protein is 10.97.

8. Gene Transfer Into *C. capitata* Using Minos Transposable Elements

Single copies of exogenous DNA can be introduced into the genome of *C. capitata* by using a germ line transformation system which utilizes the transposable element Minos to mediate precise integration of DNA at acceptable frequencies.

To provide an effective dominant selectable marker for detection of transformants, an approximately 3.7 kb NotI fragment containing the wild-type white cDNA of *C. capitata*, flanked by the *D. melanogaster* hsp 70 promoter and terminator sequences, was inserted into the NotI site of the Minos vector pMiNot which was constructed by replacing a 644 bp MscI fragment of the Minos transposase gene (nucleotides 618 to 1264 of FIGS. 2A–2C) with a NotI linker. This modified element (shown in FIG. 3A) was inserted into the E. coli vector pTZ18R (Pharmacia), creating a plasmid (pMihsCcw) having a wild-type copy of the *C. capitata* white (w) gene as a dominant visible marker.

To place the Minos transposase under heat shock control, the left-hand terminal repeat of Minos-2 was replaced by a 456 bp fragment containing the *D. melanogaster* hsp 70 promoter. This modified element (shown in FIG. 3B) was inserted into the E. coli vector pTZ18R (Pharmacia), creating the transposase-producing plasmid pHSS6hsMi.

The plasmids pMihsCcw and pHSS6hsMi were introduced into pre-blastoderm Medfly w/w embryos by a microinjection procedure similar to that used for Drosophila. For egg collecting, flies were mass-reared in population cages at 24° C. Eggs were collected at 24° C. for 60 minutes, and then were dechorionated, desiccated and microinjected at 18° C. with a mixture of 100 mg/ml helper and 400 mg/ml transposon plasmid DNA as described for Drosophila embryos (Rubin, G. M. and Spradling, A. C., *Science* 218: 348 (1982)). Modifications of the procedure were not necessary, because the eggs of the two species are similar in morphology and in resistance to desiccation.

Figure 4:
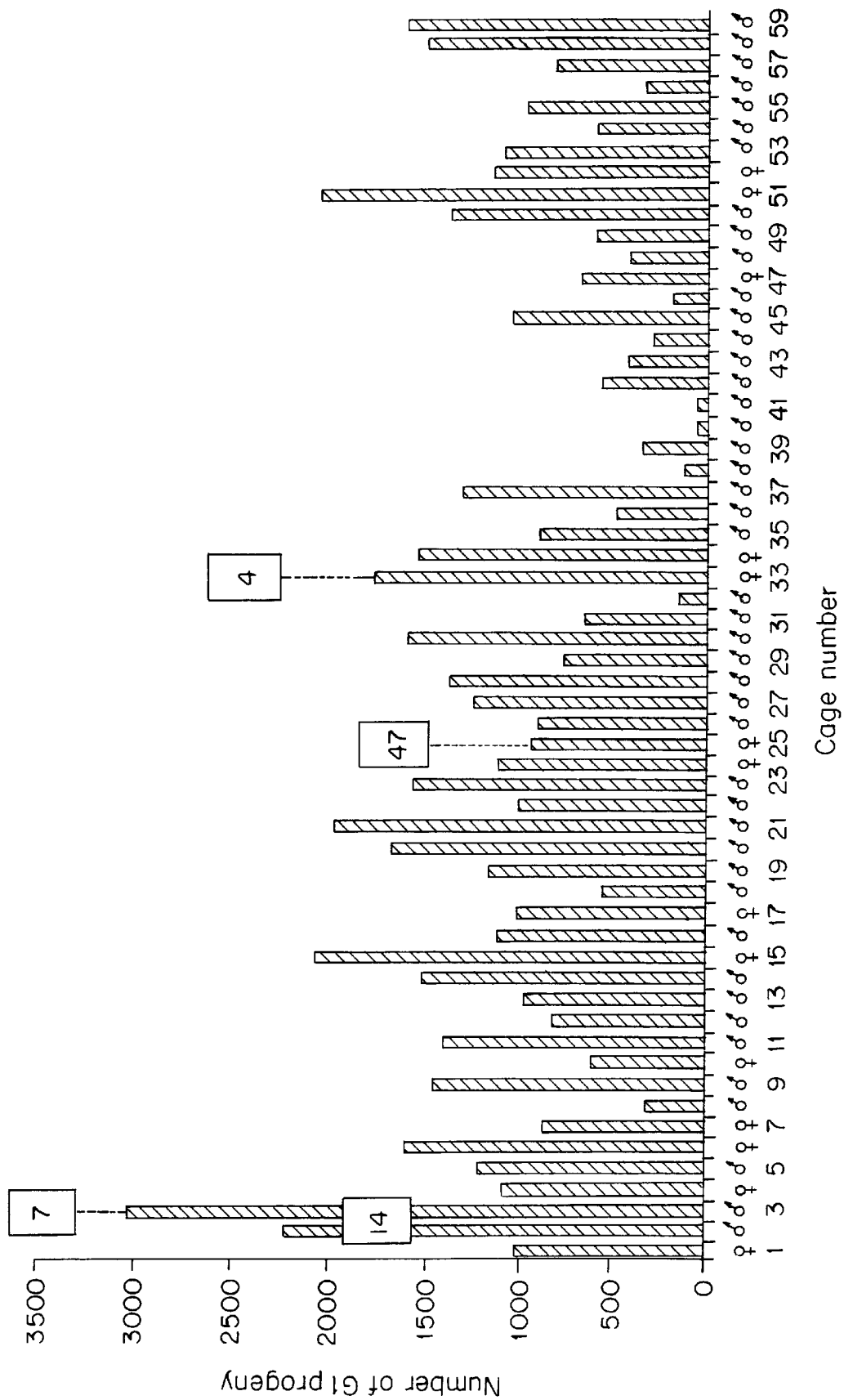
FIG. 4 is a bar graph depicting the frequencies of transformants among G1 progeny. Bars indicate the numbers of G1 flies from the individual cages. The sex of the G0 flies in each cage is indicated. The numbers above cages 1, 3, 25 and 33 indicate the w+ flies that were recovered from these cages.

A total of 3,998 embryos were injected. After injection, they were left to hatch under halocarbon oil, and first instar larvae were transferred to Petri dishes containing standard larval food (Mintzas, A. C. et al., *Dev. Biol.* 95: 492 (1983)). The 390 adults (G0 generation) resulting from injected embryos were collected within 12 hours after eclosion and back-crossed to w flies in small groups consisting of either 5 G0 males and 10 virgin w females, or 10 G0 females and 5 w males. Fifty-nine such G0 groups were reared in small plastic cages and the G1 progeny were collected and handled separately for each group. To induce expression of the w mini-gene from the Hsp70 promoter, G1 pupae were exposed daily to a 39° C. heat shock for one hour. The 62,510 G1 flies that were produced were screened for the presence of non-white eye phenotypes. As shown in FIG. 4, a total of 72 flies with colored eyes were recovered from four different cages.

The w mini-gene gives partial reversion of the phenotype. Eye color varies in strength among different transformants. The phenotype is dosage-dependent with homozygotes having stronger colors than heterozygotes. These characteristics of w markers are useful in sorting multiple insertions and in distinguishing homozygous from heterozygous transformants. The characteristics are due to low levels of expression combined with chromosomal position effects and have been observed previously in Drosophila.

To establish transformed lines, individual G1's were initially back-crossed to w flies. Single pairs of transformed G2 progeny were then mated, and their homozygous G3 progeny, recognized by their stronger $w^+$ phenotypes, were used to construct homozygous lines. Table 3 shows the results from the G1 back-crosses. In these crosses, the non-white eye ($w^+$) phenotype was inherited as a single, dominant trait.

To determine the effect of temperature on the expression of the w mini-gene, a number of G2 pupae were not subjected to the heat shock treatment. When compared to the heat-shocked cohort, G2 flies which had not been heat shocked as pupae showed either paler eye color or no eye color at all; the only exception was lines 3.1 and 3.3, which exhibited an invariant strong yellow eye phenotype. The heat shock dependence clearly showed that the flies (perhaps with the exception of 3.1 and 3.3) were true transformants, rather than revertants of the w mutation.

In cages 3 and 25, differences in the eye color phenotypes of individual G1's from the same cage were detected and bred true, suggesting that independent transformation events had occurred in the same cage.

TABLE 3

| G1 | Eye color of heterozygotes | With heat shock non-white eyes | With heat shock white eyes | Without heat shock non-white eyes | Without heat shock white eyes | Eye color of homozygotes |
|---|---|---|---|---|---|---|
| 1.1 | pale yellow | 46 | 53 | 0 | 59 | apricot |
| 1.8 | pale yellow | 220 | 274 | 0 | 77 | apricot |
| 1.12 | pale yellow | 94 | 69 | 0 | 8 | apricot |
| 3.1 | yellow | 267 | 237 | 110 | 97 | yellow |
| 3.3 | yellow | 225 | 214 | 53 | 49 | yellow |
| 3.2 | pale yellow | 132 | 118 | 0 | 76 | apricot |
| 3.6 | pale yellow | 70 | 81 | 0 | 81 | apricot |
| 25.7 | pale apricot | 119 | 156 | 116* | 91 | apricot |
| 25.8 | pink | 24 | 18 | 0 | 27 | peach |
| 25.9 | pink | 30 | 34 | 0 | 9 | peach |
| 33.2 | pale orange | 42 | 50 | ND | ND | orange |
| 33.3 | pale orange | 29 | 31 | ND | ND | orange |
| 33.4 | pale orange | 16 | 15 | ND | ND | orange |

*Eye color much weaker than with heat shock.

To determine the nature of the integration events, DNA from transformants was analyzed by Southern blot hybridizations using several restriction enzymes and two probes (see FIG. 3A), one (M) containing the Minos sequences at the ends of the transposon (which are not present in non-transformed Medfly), and another (W) containing an internal fragment of the w cDNA sequences (which is present in the endogenous w gene).

Adult genomic DNA (approximately 10 μg per lane) was digested with a restriction endonuclease, subjected to agarose gel electrophoresis, blotted onto nitrocellulose membrane filters and hybridized with $^{32}$P-labeled probes. Membranes were pre-hybridized for 6 hours at 65° C. in 7% SDS, 0.5 M phosphate buffer pH 7.4, 1 mM EDTA. Hybridization was for 12–14 hours at 65° C. in 7% SDS, 0.5 M phosphate buffer pH 7.4, 1 mM EDTA. Excess probe was removed by two 10-minute washes with 5% SDS, 40 mM phosphate buffer pH 7.4, 1 mM EDTA at 65° C. followed by a 20-minute wash at room temperature with the same buffer pre-warmed at 65° C.

Figure 3B:
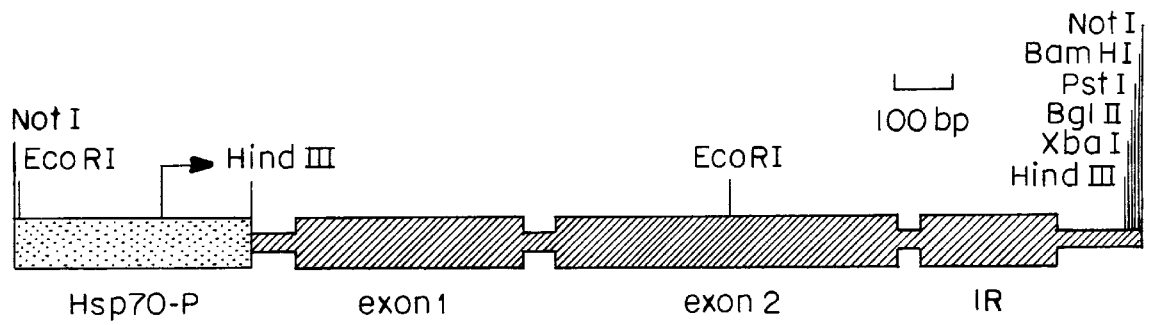
FIG. 3B is a diagram of the insert of the Minos helper plasmid pHSS6hsMi. Hatched box indicates the *D. melanogaster* Hsp70 promoter (Hsp70-P) sequence. Salient restriction sites are shown. Exon 1 and exon 2 are also referred to herein as open reading frame 1 (ORF1) and open reading frame 2 (ORF2), respectively. IR indicates the right-hand terminal inverted repeat.

DNA from lines 3.1, 3.2, 3.3 and 3.6 was cut with SalI and hybridized with a 1 kb HhaI fragment containing Minos sequences present in pMiNot (M probe of FIG. 3A).

DNA from the recipient w strain and from lines 3.1, 3.2, 3.3 and 3.6 was cut with HincII, and probed with a SalI/XhoI fragment containing 1.5 kb of Medfly w cDNA sequences (W probe of FIG. 3A) and with the M probe. Between the two hybridizations the filter was dehybridized by washing with boiling 0.5% SDS solution for 2 minutes.

In Drosophila, insertions of elements like Minos can occur at many different chromosomal sites, and are characterized by precise integration extending through the terminal inverted repeats of the element without transposition of any flanking plasmid DNA. The results of M-hybridized SalI digests document that the events in the Medfly are of the same nature. The transposon has inserted variable host DNA sites, and no significant (>0.2 kb) flanking plasmid DNA to the right of the transposon can be present, because this would have been signaled by the presence of a 2.9 kb band. The results also confirm that two independent events have occurred in cage 3, one represented by lines 3.1 and 3.3 and the other by lines 3.2 and 3.6 (cf. Table 3). These conclusions were also confirmed with HincII digests. Similarly, blots of HincII digests hybridized with the W probe showed the two endogenous w gene bands, plus a third novel band that is characteristic of the insertion event (3.1/3.3 or 3.2/3.6). The shortest band is longer than the 1.9 kb band that would have been expected if the HincII site, 0.2 kb to the right of the Minos end (see FIG. 3A) had been present. The same HincII blot hybridized with the M probe showed that the shortest band is longer than the 1.1 kb band that would have been expected if plasmid sequences to the left of the transposon were present. These results were confirmed with W-hybridized SalI digests.

To assess the integrity of the internal part of the transposon, restriction analysis using EcoRI was performed in three lines derived from cage 25. DNA from strains 25.7, 25.8 and 25.9 was cut with EcoRI and hybridized with the W and M probe sequentially. In addition to the transformants showing non-white eye phenotypes white-eyed siblings (25.9-w, 25.8-w, 25.7-w) were included in this analysis. The results of the hybridization with the W probe indicate that the entire 3.7 kb fragment containing the Hsp70/w marker fusion is present in the $w^+$ transformants. Hybridization of the same filter with the M probe, which detects "chimeric" end fragments, showed that lines 25.8 and 25.9 contain the same, single insertion of the transposon. The pattern in 25.7 is consistent with the presence of two insertions, neither identical to the 25.8/25.9 event. One of these insertions, defined by the ~3 kb and ~5.5 kb bands, is also present in the white-eyed siblings of the 25.7 flies. This, presumably, represents a "silent" insertion that does not express the phenotype either due to an undetected lesion in the transposon, or because the transposon has integrated into a silent (perhaps heterochromatic) genomic region.

Restriction analysis of the transformants revealed that, as predicted by the phenotypes (Table 3), two independent transformants were represented among the G1 progeny of cage 3, two in cage 25, and one in cage 33 (Data for transformants from cage 33 are not shown. The restriction patterns of three G1's from cage 1 were identical to these of the 3.2/3.6 event. Evidently, a G0 male present in cage 3 had mated with a G0 female of cage 1, before the G0 flies were sorted into cages.) Only one of these 5 transformants (25.7) had a second (phenotypically silent) event in the same germ line. The different transformants from the same cages are derived either from single or multiple G0 parents. The overall frequency of phenotypically detectable transformation events (5/390 G0 adults) is sufficient for producing several transformants from a single experiment since thousands of embryos can be injected and hundreds of G0 adults can be obtained within a week using a relatively simple experimental setup.

To confirm the presence of a single Minos insertion in transformant 3.1, third instar larva salivary gland polytene chromosomes were prepared and in situ hybridization were performed essentially as described previously (Zacharopoulou, A., et al., *Chromosoma* 101: 448 (1992)). The 3.7 kb NotI fragment containing the Hsp70/w minigene fusion was used as probe. Hybridization to polytene chromosomes of salivary glands from transformed third instar larvae confirmed the presence of single Minos insertions, allowing their cytological localization.

Example 2
Materials and Methods

1. Transfection of Mammalian Cells Human HeLa cells and green monkey COS1 cells were cultured at 37° C. in an atmosphere containing 4% $CO_2$ in DMEM supplemented with 10% fetal calf serum (FCS) and 50 µg/ml gentamycin. HeLa cells were seeded onto 60 mm dishes (300,000 cells per dish) and COS1 cells were seeded onto 6-well plates (200,000 cells per well) one day prior to transfection.

2. HeLa Cell Tranfections

HeLa cells were transfected with Qiagen (Qiagen) and Elutip (Schleicher and Schuell)-purified supercoiled plasmid DNA in 2.5 ml DMEM supplemented with 2% FCS and 50 µg/ml gentamycin and 0.5 ml of a calcium/HBS precipitant, according to the calcium chloride procedure described by Sambrook et al. (*Molecular Cloning: A Laboratory Manual*, Cold Spring Harbor Laboratory Press, Plainview, N.Y., (1989)).

Figure 5:
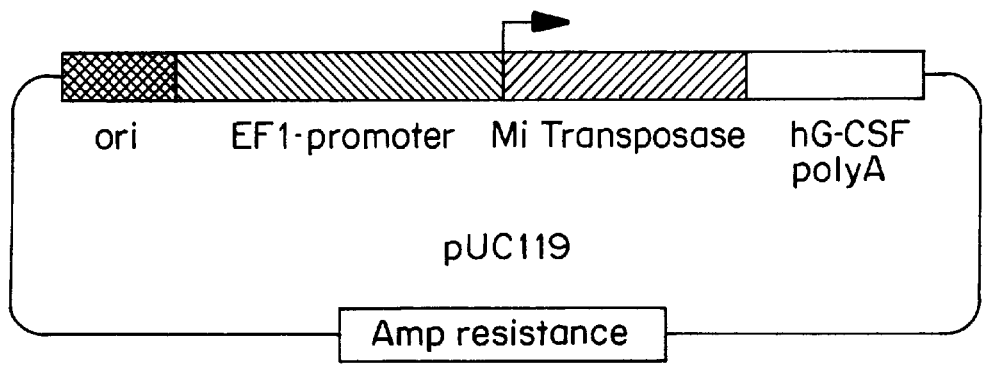
FIG. 5 is a diagram of the helper plasmid bEF1/ILMi. The arrow represents the transcription start site and indicates the direction of transcription of the Minos (Mi) transposase gene which is linked to the human translation elongation factor (EF1)-promoter. The fragment containing the EF1 promoter also comprises a 943 bp intron in the 5' untranslated region which provides an intron for the transposase RNA transcript. Upstream from the EF-1 promoter is the SV40 origin of replication (ori). The 3' end of the Minos transposase gene contains a polyadenylation signal from the human granulocyte colony-stimulating factor gene (hG-CSF).
Figure 6:
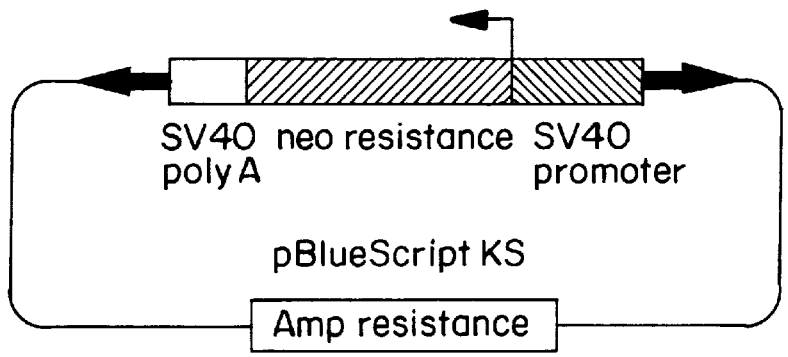
FIG. 6 is a diagram of the transposon plasmid pMiLRneo. The arrowhead represents the transcription start site and indicates the direction of transcription. The plasmid contains the neomycin (neo) resistance gene under the control of the early SV40 promoter, flanked by two inverted repeats of the Minos transposable element (bolded arrows).
Figure 7:
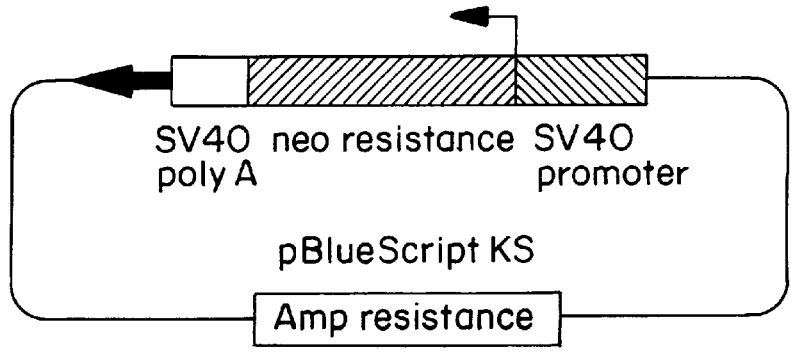
FIG. 7 is a diagram of the plasmid pMiLneo. The arrowhead represents the transcription start site and indicates the direction of transcription. The pMiLneo plasmid is derived from pMiLRneo (FIG. 6) by deletion of the right hand repeat of Minos to generate the defective transposon "wings clipped". The remaining left hand inverted repeat is indicated by the bolded arrow.

Hela cell were transfected with either 8 µg of transposon plasmid pMiLRneo (FIG. 6) alone; a mixture of 8 µg of the transposon plasmid pMiLRneo (FIG. 6) and 2 µg of the helper plasmid pEF1/ILMi (FIG. 5); or a mixture of 8 µg of the "wings clipped" plasmid pMiLneo (FIG. 7) and 2 µg of the helper plasmid pEF1/ILMi (FIG. 5). The "wings clipped" plasmid includes a modified Minos transposon in which one of the inverted repeats has been excised.

The pMiLneo transposon plasmid and the "wings clipped" plasmid include a selectable neomycin (neo) resistance gene, which is under the control of the SV40 early promoter (e.g., operably linked). The neo gene encodes a prokaryotic aminoglycoside phosphotransferase that detoxifies the antibiotic G418 which blocks protein synthesis in eukaryotic and prokaryotic cells, thereby allowing for selection and growth of colonies containing inserts (transfected cells).

After 16 hours of incubation with DNA, the cells were washed twice with serum-free DMEM and re-fed with 4 ml of serum containing (10% FCS) DMEM. Two days post-transfection, the cells were treated with trypsin and seeded onto 150 mm (Experiment #1, Table 4) or 90 mm (Experiments #2 and #3, Table 4) dishes with DMEM-10% FCS containing 600 µg/ml G418 (Gibco-BRL). After 15 days of selection, cell clones were either isolated and expanded into individual cultures, or fixed in a solution containing 10% (v/v) formaldehyde in PBS for 15 minutes. Fixed cells were stained with 2% (w/v) methylene blue in PBS and colonies counted.

3. COS Cell Transfections

COS1 cells were prepared for transfection. Transfection selection was performed as described for the HeLa cells, except that COS cells were transfected with a mixture of 3 µg supercoiled pEF1/ILMi helper plasmid DNA (FIG. 5) and 3 µg supercoiled pQB125 (Quantum) plasmid DNA. Colonies were fixed in 10% formaldehyde in PBS. Expression and cellular localization of the plasmid DNA encoding the transposase was determined by indirect immunocytochemical techniques using a polyclonal antisera for Minos transposase and a rhodamine-conjugated goat anti-rabbit antibody.

Results

1. Transposase-Induced Stable Transfection of HeLa Cells With a Minos Transposon.

As shown in Table 4, HeLa cells transfected with transposon plasmid pMiRneo in the presence of the helper plasmid pEF-1ILMi, which encodes a transposase, resulted in a 19-fold (Experiment #1), a 18-fold (Experiment #2) and a 14.5-fold (Experiment #3) increase in the rate of recovery of stable transfectants, compared to transfection with the transposon plasmid pMiLRneo alone.

The transfection depends upon the presence of two functional Minos inverted repeats in the transposon plasmid, since transfection in the presence of the "wings clipped" transposon and the helper plasmid results in numbers of colonies roughly equivalent to the number of background colonies produced by transfection with transposon plasmid alone.

Moreover, the percentage of HeLa cell transfected by the Minos-based system was high (e.g., 2.5% in Experiment #1) compared to previously described methods used to transfect mammalian cells. Existing transfection methods generally result in very low percentages of stably transfected cells. In the present experiments, between $10^{-4}$ and $10^{-3}$ stably transfected cells were obtained by using the calcium co-precipitation method as described in Ausubel et al., supra. (see Chapters 9.1.11 and 9.5.1 (1998)). For example, in Experiment #1, the stable transfection efficiency was 25- to 250-fold higher than that obtained by conventional methods. Thus, the present invention is a new and improved method for transfecting cells including mammalian cells.

TABLE 4

| EXPERIMENT | Transposon | | Transposon + Helper | | "wings clipped" + Helper | |
|---|---|---|---|---|---|---|
| | A | B | A | B | A | B |
| #1 | 800 | 0.13 | ~15,000 | 2.5 | – | – |
| #2 | 250 | 0.041 | 4,500 | 0.75 | – | – |
| #3 | 200 | 0.033 | 2,900 | 0.48 | 300 | 0.020 |

A = Number of Transfected Colonies
B = Percent of Cells Transfected

These data show that co-transfection of a human cell line with a plasmid carrying a Minos transposon and the Minos transposase gene results in integration of a nucleic acid sequence.

These data show that both transposase and the presence of two Minos ends are necessary for integration into the genome of cells (e.g., mammalian cells). Therefore, the data show that the integration effect of the Minos transposase is a result of its specific enzymatic function.

For example, in insect cells, transposases of Type II mobile elements like the Minos transposase, function by binding at or near the inverted repeats of the transposon and catalyzing the precise excision of the entire transposon (i.e. the DNA flanked by and including the inverted repeats) from its position and precise re-insertion into DNA. Like other known elements belonging to the same family of transposons with Minos, insertion of the Minos transposon into DNA is not entirely random. The element inserts at a TA dinucleotide via a mechanism that causes duplication of the target TA. In this way, transposase-mediated integrations of Minos can be characterized by the presence of intact inverted repeats flanked by TA dinucleotides. Consequently, the molecular basis of the Minos transposon insertions in the stably transfected HeLa cells can be determined by Southern blot analysis of the DNA from G418 resistant colonies, and can be confirmed by cloning and sequencing of individual insertions from these sublines.

2. Expression and Nuclear Localization of Minos Transposase in Transiently Transfected COS1 Cells Minos transposase was localized in the nuclei of the cells, documenting expression of the Minos transposase and transport into the nuclei. Nuclear localization of Minos transposase is consistent with the function of Minos as a transposase and the presence of several nuclear localization signals consisting of stretches of amino acid residues with basic side chains in its primary amino acid sequence.

Equivalents

Those skilled in the art will recognize or be able to ascertain, using no more than routine experimentation, many equivalents to the specific embodiments of the invention described herein. Such equivalents are intended to be encompassed by the following claims.

What is claimed:

1. A method for integrating a nucleic acid sequence of interest into the chromosome of a cell, comprising the steps of:

a) providing an isolated transposable element having a nucleic sequence which hybridizes to the DNA sequence of SEQ ID NO:1 or SEQ ID NO:4 in a buffered solution of 0.9 M NaCl, at a temperature of 55° C., the isolated transposable element being modified to include the nucleic acid sequence of interest flanked by the inverted terminal repeats of the isolated transposable element; and b) producing a sample by introducing the isolated transposable element of step a) into the cell in the presence of:

i) a transposase protein encoded by a nucleic acid sequence which hybridizes to the DNA sequence of SEQ ID NO: 1 or SEQ ID NO:4 in a buffered solution of 0.9 M NaCl, at a temperature of 55° C.; or ii) an expressible nucleic acid sequence encoding a transposase protein, the expressible nucleic acid sequence being characterized by the ability to hybridize to the DNA sequence of SEQ ID NO:1 or SEQ ID NO:4 in a buffered solution of 0.9 M NaCl, at a temperature of 55° C.

2. The method of claim 1 further comprising selecting from the sample obtained in step b) cells in which the transposable element has integrated into the chromosome.

3. The method of claim 1, wherein the expressible nucleic acid sequence encoding the transposase protein is integrated into the genome of the cell prior to the transposable element containing the nucleic acid sequence of interest.

4. The method of claim 1, wherein the cell is an animal somatic or germ line cell.

5. The method of claim 1, wherein the nucleic acid sequence of interest encodes a protein of interest.

6. The method of claim 1, wherein the isolated transposable element is modified to include the nucleic acid sequence of interest operably linked to a promoter and an indicator gene under the control of said promoter.

7. The method of claim 6, wherein the indicator gene is selected from the group consisting of:
   a) a reporter gene; and
   b) a selectable marker gene.

8. The method of claim 1, wherein the nucleic acid sequence of interest is selected from the group consisting of:
   a) a reporter gene; and
   b) a selectable marker gene.

9. The method of claim 1, wherein the transposable element and the nucleic acid sequence encoding the transposase protein are incorporated into a viral vector.

10. A method for inducing a mutation in a cell, comprising the steps of:
   a) providing an isolated transposable element having a nucleic acid sequence which hybridizes to the DNA sequence of SEQ ID NO:1 or SEQ ID NO:4 in a buffered solution of 0.9 M NaCl, at a temperature of 55° C.;
   b) introducing the isolated transposable element of step a) into the cell in the presence of:
      i) a transposase protein encoded by a nucleic acid sequence which hybridizes to the DNA sequence of SEQ ID NO:1 or SEQ ID NO:4 in a buffered solution of 0.9 M NaCl, at a temperature of 55° C.; or
      ii) an expressible nucleic acid sequence encoding a transposase protein, the expressible nucleic acid sequence being characterized by the ability to hybridize to the DNA sequence of SEQ ID NO:1 or SEQ ID NO;4 in a buffered solution of 0.9 M NaCl, at a temperature of 55° C; and
   c) screening for cells including a transposable element-induced mutation.

11. The method of claim 10, wherein the transposable element is modified to include a promoter operably linked to an indicator gene under the control of said promoter flanked by the inverted terminal repeats of the isolated transposable element.

12. The method of claim 10, wherein the transposable element and nucleic acid sequence encoding the transposase protein are incorporated into a viral vector.

13. A method for isolating a gene of interest in a cell which includes a mutation, comprising the steps of:
   a) providing an isolated transposable element having a nucleic acid sequence which hybridizes to the DNA sequence of SEQ ID NO:1 or SEQ ID NO:4 in a buffered solution of 0.9 M NaCl, at a temperature of 55° C., the isolated transposable element being modified to include a promoter operably linked to an indicator gene under the control of said promoter flanked by the inverted terminal repeats of the isolated transposable element;
   b) producing a sample by introducing the isolated transposable element of step a) into a population of cells in the presence of:
      i) a transposase protein encoded by a nucleic acid sequence which hybridizes to the DNA sequence of SEQ ID NO:1 or SEQ ID NO:4 in a buffered solution of 0.9 M NaCl, at a temperature of 55° C.; or
      ii) an expressible nucleic acid sequence encoding a transposase protein, the expressible nucleic acid sequence being characterized by the ability to hybridize to the DNA sequence of SEQ ID NO:1 or SEQ ID NO:4 in a buffered solution of 0.9 M NaCl, at a temperature of 55° C.;
   c) detecting expression of the indicator gene in the sample obtained in step b), thereby identifying cells in which the transposable element has integrated into tie genome of the cells;
   d) selecting from among the cells identified in step c) cells which have a mutation in a gene of interest; and
   e) isolating the gene of interest which includes the mutation from the cells identified in step d).

14. The method of claim 13, wherein the indicator gene is a selected from the group consisting of:
   a) a selectable marker gene; and
   b) a reporter gene.

15. The method of claim 13, wherein the transposable element and nucleic acid sequence encoding the transposase protein are incorporated into a viral vector.

16. The method of claim 13, wherein the cell is an animal somatic or germ line cell.

17. A method for selecting an insertional mutation in a gene in a cell, comprising the steps of:
   a) providing an isolated transposable element having a nucleic acid sequence which hybridizes to the DNA sequence of SEQ ID NO:1 or SEQ ID NO:4 in a buffered solution of 0.9 M NaCl, at a temperature of 55° C., the isolated transposable element being modified to include a minimal promotor operably linked to an indicator gene flanked by the inverted terminal repeats of the isolated transposable element;
   b) producing a sample by introducing the isolated transposable element of step a) into a population of cells in the presence of:
      i) a transposase protein encoded by a nucleic acid sequence which hybridizes to the DNA sequence of SEQ ID NO:1 or SEQ ID NO:4 in a buffered solution of 0.9 M NaCl, at a temperature of 55° C.; or
      ii) an expressible nucleic acid sequence encoding a transposase protein, the expressible nucleic acid sequence being characterized by the ability to hybridize to the DNA sequence of SEQ ID NO:1 or SEQ ID NO:4 in a buffered solution of 0.9 M NaCl, at a temperature of 55° C.;
   c) detecting expression of the indicator gene in the sample obtained in step b), thereby identifying cells including a transposable clement-induced mutation in a gene; and d) isolating from the cells identified in step c) the gene including the transposable element-induced mutation.

18. The method of claim 17, wherein the minimal promoter is a TATA box.

19. The method of claim 17, wherein the transposable element and nucleic acid sequence encoding the transposase protein are incorporated into a viral vector.

20. The method of claim 17, wherein the cell is an animal somatic or germ line cell.

21. A method for selecting an insertional mutation in a gene in a cell, comprising the steps of:
   a) providing an isolated transposable element having a nucleic acid sequence which hybridizes to the DNA sequence of SEQ ID NO:1 or SEQ ID NO:4 in a buffered solution of 0.9 M NaCl, at a temperature of 55° C., the isolated transposable element being modified to include a splice acceptor site operably linked to an indicator gene flanked by the inverted terminal repeats of the isolated transposable element;
   b) producing a sample by introducing the isolated transposable element of step a) into a population of cells in the presence of:
      i) a transposase protein encoded by a nucleic acid sequence which hybridizes to the DNA sequence of SEQ ID NO:1 or SEQ ID NO:4 in a buffered solution of 0.9 M NaCl, at a temperature of 55° C.; or
      ii) an expressible nucleic acid sequence encoding a transposase protein, the expressible nucleic acid sequence being characterized by the ability to hybridize to the DNA sequence of SEQ ID NO:1 or SEQ ID NO:4 in a buffered solution of 0.9 M NaCl, at a temperature of 55° C.;
   c) detecting expression of the indicator gene in the sample obtained in step b), thereby identifying cells including a transposable element-induced mutation in a gene; and
   d) isolating from the cells identified in step c) the gene including the transposable element-induced mutation.

22. The method of claim 21, wherein the transposable element and expressible nucleic acid sequence encoding the transposase protein are incorporated into a viral vector.

23. The method of claim 21, wherein the cell is an animal somatic or germ line cell.

24. A method for reversing a mutation in a gene of interest, obtained according to the method of claim 13, comprising introducing into cells identified in step d):
   i) a transposase protein encoded by a nucleic acid sequence which hybridizes to the DNA sequence of SEQ ID NO:1 or SEQ ID NO:4 in a buffered solution of 0.9 M NaCl, at a temperature of 55° C.; or
   ii) an expressible nucleic acid sequence encoding a transposase protein, the expressible nucleic acid sequence being characterized by the ability to hybridize to the DNA sequence of SEQ ID NO: 1 or SEQ ID NO:4 in a buffered solution of 0.9 M NaCl, at a temperature of 55° C.

25. The method of claim 24, wherein the nucleic acid sequence encoding the transposase protein is incorporated into a viral vector.

26. The method of claim 24, wherein the cells are animal somatic or germ line cells.

27. A method for reversing a mutation in a gene, obtained according to the method of claim 17, comprising introducing into cells identified in step c):
   i) a transposase protein encoded by a nucleic acid sequence which hybridizes to the DNA sequence of SEQ ID NO:1 or SEQ ID NO:4 in a buffered solution of 0.9 M NaCl, at a temperature of 55° C.; or an expressible nucleic acid sequence encoding a transposase protein, the expressible nucleic acid sequence being characterized by the ability to hybridize to the DNA sequence of SEQ ID NO:1 or SEQ ID NO:4 in a buffered solution of 0.9 M NaCl, at a temperature of 55° C.; and
   ii) screening for cells which do not include the transposable clement-induced mutation.

28. The method of claim 27, wherein the nucleic acid sequence encoding the transposase protein is incorporated into a viral vector.

29. The method of claim 27, wherein the cells are animal somatic or germ line cells.

30. A method for reversing a mutation in a gene, obtained according to the method of claim 21, comprising introducing into cells identified in step c):
   i) a transposase protein encoded by a nucleic acid sequence which hybridizes to the DNA sequence of SEQ ID NO:1 or SEQ ID NO:4 in a buffered solution of 0.9 M NaCl, at a temperature of 55° C.; or an expressible nucleic acid sequence encoding a transposase protein, the expressible nucleic acid sequence being characterized by the ability to hybridize to the DNA sequence of SEQ ID NO:1 or SEQ ID NO:4 in a buffered solution of 0.9 M NaCl, at a temperature of 55° C.; and
   ii) screening for cells which do not include the transposable element-induced mutation.

31. The method of claim 30, wherein the nucleic acid sequence encoding the transposase protein is incorporated into a viral vector.

32. The method of claim 30, wherein the cells are animal somatic or germ line cells.

33. A method for introducing a reversible mutation in a gene of interest in a cell, comprising the steps of:
   a) providing an isolated transposable element having a nucleic acid sequence which hybridizes to the DNA sequence of SEQ ID NO:1 or SEQ ID NO:4 in a buffered solution of 0.9 M NaCl, at a temperature of 55° C., the isolated transposable element being modified to include:
      i) a promoter operably linked to an indicator gene flanked by the inverted terminal repeats of the isolated transposable element; or
      ii) a minimal promoter operably linked to an indicator gene flanked by the inverted terminal repeats of the isolated transposable element; or
      iii) a splice acceptor site operably linked to an indicator gene flanked by the inverted terminal repeats of the isolated transposable element;
   b) introducing the isolated transposable element of step a) into a gene of interest, thereby producing a mutated gene;
   c) introducing the mutated gene of step b) into a population of cells under conditions sufficient for homologous recombination between the mutated gene and the corresponding endogenous gene, thereby producing a sample; and
   d) selecting from the sample obtained in step c) cells in which the endogenous gene has been replaced the mutated gene.

34. The method of claim 33, wherein the indicator gene is selected from the group consisting of:
   a) a reporter gene; and
   b) a selectable marker gene.

35. The method of claim 33, wherein the minimal promoter is a TATA box.

36. The method of claim 33, wherein the transposable element is incorporated into a viral vector.

37. The method of claim 33, wherein the cell is an animal somatic or germ line cell.

38. A method for reversing a mutation in a gene, obtained according to the method of claim 33, comprising introducing into cells identified in step d):
   i) a transposase protein encoded by a nucleic acid sequence which hybridizes to the DNA sequence of SEQ ID NO:1 or SEQ ID NO:4 in a buffered solution of 0.9 M NaCl, at a temperature of 55° C.; or an expressible nucleic acid sequence encoding a transposase protein, the expressible nucleic acid sequence being characterized by the ability to hybridize to the DNA sequence of SEQ ID NO:1 or SEQ ID NO:4 in a buffered solution of 0.9 M NaCl, at a temperature of 55° C.; and
   ii) screening for cells which do not include the mutation.

39. The method of claim 38, wherein the nucleic acid sequence encoding the transposase protein is incorporated into a viral vector.

40. The method of claim 38, wherein the cells are animal somatic or germ line cells.

41. A method for inducing loss of a nucleic acid sequence of interest integrated into the chromosome of a cell according to the method of claim 2, comprising introducing into the cells identified:
   i) a transposase protein encoded by a nucleic acid sequence which hybridizes to the DNA sequence of SEQ ID NO:1 or SEQ ID NO:4 in a buffered solution or 0.9 M NaCl, at a temperature of 55° C.; or an expressible nucleic acid sequence encoding a transposase protein, the expressible nucleic acid sequence being characterized by the ability to hybridize to the DNA sequence of SEQ ID NO:1 or SEQ ID NO:4 in a buffered solution of 0.9 M NaCl, at a temperature of 55° C.; and
   ii) screening for cells which do not include the nucleic acid sequence of interest integrated into the chromosome.

42. The method of claim 41, wherein the nucleic acid sequence encoding the transposase protein is incorporated into a viral vector.

43. The method of claim 41, wherein the cells are animal somatic or germ line cells.

44. The method of claim 41, wherein the cells are somatic or germ line cells of a transgenic animal.

45. The method of claim 41, wherein the isolated transposable element is modified to include the gene of interest operably linked to a promoter and an indicator gene under the control of said promoter.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
       (A) LENGTH: 1775 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:1:

```
ACGAGCCCCA ACCACTATTA ATTCGAACAG CATGTTTTTT TTGCAGTGCG CAATGTTTAA      60

CACACTATAT TATCAATACT ACTAAAGATA ACACATACCA ATGCATTTCG TCTCAAAGAG     120

AATTTTATTC TCTTCACGAC GAAAAAAAAA GTTTTGCTCT ATTTCCAACA ACAACAAAAA     180

TATGAGTAAT TTATTCAAAC GGTTTGCTTA AGAGATAAGA AAAAAGTGAC CACTATTAAT     240

TCGAACGCGG CGTAAGCTTA CCTTAATCTC AAGAAGAGCA AAACAAAAGC AACTAATGTA     300

ACGGAATCAT TATCTAGTTA TGATCTGCAA ATAATGTCAC AATACAGCAT GCAAAAAAAT     360

TTTAGATTGC TGCAGATCAG TAGAAGTTTA GCAACGATGG TTCGTGGTAA ACCTATTTCT     420

AAAGAAATCA GAGTATTGAT TAGGGATTAT TTTAAATCTG GAAAGACACT TACGGAGATA     480

AGCAAGCAAT TAAATTTGCC TAAGTCGTCT GTGCATGGGG TGATACAAAT TTTCAAAAAA     540

AATGGGAATA TTGAAAATAA CATTGCGAAT AGAGGCCGAA CATCAGCAAT AACACCCCGC     600

GACAAAAGAC AACTGGCCAA AATTGTTAAG GCTGATCGTC GCCAATCTTT GAGAAATTTG     660

GCTTCTAAGT GGTCGCAGCA ATTGGCAAAA CTGTCAAGCG AGAGTGGACG CGACAAATTA     720

AAAAGTATTG GATATGGTTT TTATAAAGTA TGTTTTGTTA TTACCTGTGC ATCGTACCCA     780

ATAACTTACT CGTAATCTTA CTCGTAGGCC AAGGAAAAAC CCTTGCTTAC GCTTCGTCAA     840

AAAAAGAAGC GTTTGCAATG GGCTCGGGAA AGGATGTCTT GGACTCAAAG GCAATAGGAT     900

ACCATCATAT TCAGCGATGA AGCTAAATTT GATGTTAGTG TCGGCGATAC GAGAAAACGC     960

GTCATCCGTA AGAGGTCAGA AACATACCAT AAAGACTGCC TTAAAAGAAC AACAAAGTTT    1020

CCTGCGAGCA CTATGGTATG GGGATGTATG TCTGCCAAAG GATTAGGAAA ACTTCATTTC    1080
```

-continued

```
ATTGAAGGGA CAGTTAATGC TGAAAAATAT ATTAATATTT TACAAGATAG TTTGTTGCCA    1140

TCAATACCAA AACTATCAGA TTGCGGTGAA TTCACTTTTC AGCAGGACGG AGCATCATCG    1200

CACACAGCCA AGCGAACCAA AAATTGGCTG CAATATAATC AAATGGAGGT TTTAGATTGG    1260

CCATCAAATA GTCCAGATCT AAGCCCAATT GAAAATATTT GGTGGCTAAT GAAAAACCAG    1320

CTTCGAAATG AGCCACAAAG GAATATTTCT GACTTGAAAA TCAAGTTGCA AGAGATGTGG    1380

GACTCAATTT CTCAAGAGCA TTGCAAAAAT TTGTTAAGCT CAATGCCAAA ACGAGTTAAA    1440

TGCGTAATGC AGGCCAAGGG CGACGTTACA CAATTCTAAT ATTAATTAAA TTATTGTTTT    1500

AAGTATGATA GTAAATCACA TTACGCCGCG TTCGAATTAA TAGTGGTCAC TTTTTTCTTA    1560

TCTCTTAAGC AAACCGTTTG AATAAATTAC TCATATTTTT GTTGTTGTTG GAAATAGAGC    1620

AAAACTTTTT TTTTCGTCGT GAAGAGAATA AAATTCTCTT TGAGACGAAA TGCATTGGTA    1680

TGTGTTATCT TTAGTAGTAT TGATAATATA GTGTGTTAAA CATTGCGCAC TGCAAAAAAA    1740

ACATGCTGTT CGAATTAATA GTGGTTGGGG CTCGT                              1775
```

(2) INFORMATION FOR SEQ ID NO:2:

(i) SEQUENCE CHARACTERISTICS:
        (A) LENGTH: 1775 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

```
ACGAGCCCCA ACCACTATTA ATTCGAACAG CATGTTTTTT TTGCAGTGCG CAATGTTTAA      60

CACACTATAT TATCAATACT ACTAAAGATA ACACATACCA ATGCATTTCG TCTCAAAGAG     120

AATTTTATTC TCTTCACGAC GAAAAAAAAA GTTTTGCTCT ATTCCAACA ACAACAAAAA      180

TATGAGTAAT TTATTCAAAC GGTTTGCTTA AGAGATAAGA AAAAAGTGAC CACTATTAAT     240

TCGAACGCGG CGTAAGCTTA CCTTAATCTC AAGAAGAGCA AAACAAAAGC AACTAATGTA     300

ACGGAATCAT TATCTAGTTA TGATCTGCAA ATAATGTCAC AATACAGCAT GCAAAAAAAT     360

TTTAGATTGC TGCAGATCAG TAGAAGTTTA GCAACGATGG TTCGTGGTAA ACCTATTTCT     420

AAAGAAATCA GAGTATTGAT TAGGGATTAT TTTAAATCTG GAAAGACACT TACGGAGATA     480

AGCAAGCAAT TAAATTTGCC TAAGTCGTCT GTGCATGGGG TGATACAAAT TTTCAAAAAA     540

AATGGGAATA TTGAAAATAA CATTGCGAAT AGAGGCCGAA CATCAGCAAT AACACCCCGC     600

GACAAAAGAC AACTGGCCAA AATTGTTAAG GCTGATCGTC GCCAATCTTT GAGAAATTTG     660

GCTTCTAAGT GGTCGCAGCA ATTGGCAAAA CTGTCAAGCG AGAGTGGACG CGACAAATTA     720

AAAAGTATTG GATATGGTTT TTATAAAGTA TGTTTTGTTA TTACCTGTGC ATCGTACCCA     780

ATAACTTACT CGTAATCTTA CTCGTAGGCC AAGGAAAAAC CCTTGCTTAC GCTTCGTCAA     840

AAAAAGAAGC GTTTGCAATG GGCTCGGGAA AGGATGTCTT GGACTCAAAG GCAATGGGAT     900

ACCATCATAT TCAGCGATGA AGCTAAATTT GATGTTAGTG TCGGCGATAC GAGAAAACGC     960

GTCATCCGTA AGAGGTCAGA AACATACCAT AAAGACTGCC TTAAAAGAAC AACAAAGTTT    1020

CCTGCGAGCA CTATGGTATG GGGATGTATG TCTGCCAAAG GATTAGGAAA ACTTCATTTC    1080

ATTGAAGGGA CAGTTAATGC TGAAAAATAT ATTAATATTT TACAAGATAG TTTGTTGCCA    1140

TCAATACCAA AACTATTAGA TTGCGGTGAA TTCACTTTTC AGCAGGACGG AGCATCATCG    1200

CACACAGCCA AGCGAACCAA AAATTGGCTG CAATATAATC AAATGGAGGT TTTAGATTGG    1260
```

-continued

```
CCATCAAATA GTCCAGATCT AAGCCCAATT GAAAATATTT GGTGGCTAAT GAAAAACCAG      1320

CTTCGAAATG AGCCACAAAG GAATATTTCT GACTTGAAAA TCAAGTTGCA AGAGATGTGG      1380

GACTCAATTT CTCAAGAGCA TTGCAAAAAT TTGTTAAGCT CAATGCCAAA ACGAGTTAAA      1440

TGCGTAATGC AGGCCAAGGG CGACGTTACA CAATTCTAAT ATTAATTAAA TTATTGTTTT      1500

AAGTATGATA GTAAATCACA TTACGCCGCG TTCGAATTAA TAGTGGTCAC TTTTTTCTTA      1560

TCTCTTAAGC AAACCGTTTG AATAAATTAC TCATATTTTT GTTGTTGTTG GAAATAGAGC      1620

AAAACTTTTT TTTTCGTCGT GAAGAGAATA AAATTCTCTT TGAGACGAAA TGCATTGGTA      1680

TGTGTTATCT TTAGTAGTAT TGATAATATA GTGTGTTAAA CATTGCGCAC TGCAAAAAAA      1740

ACATGCTGTT CGAATTAATA GTGGTTGGGG CTCGT                                1775
```

(2) INFORMATION FOR SEQ ID NO:3:

(i) SEQUENCE CHARACTERISTICS:
        (A) LENGTH: 1775 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

```
ACGAGCCCCA ACCACTATTA ATTCGAACAG CATGTTTTTT TTGCAGTGCG CAATGTTTAA        60

CACACTATAT TATCAATACT ACTAAAGATA ACACATACCA ATGCATTTCG TCTCAAAGAG       120

AATTTTATTC TCTTCACGAC GAAAAAAAAA GTTTTGCTCT ATTTCCAACA ACAACAAAAA       180

TATGAGTAAT TTATTCAAAC GGTTTGCTTA AGAGATAAGA AAAAAGTGAC CACTATTAAT       240

TCGAACGCGG CGTAAGCTTA CCTTAATCTC AAGAAGAGCA AAACAAAAGC AACTAATGTA       300

ACGGAATCAT TATCTAGTTA TGATCTGCAA ATAATGTCAC AATACAGCAT GCAAAAAAAT       360

TTTAGATTGC TGCAGATCAG TAGAAGTTTA GCAACGATGG TTCGTGGTAA ACCTATTTCT       420

AAAGAAATCA GAGTATTGAT TAGGGATTAT TTTAAATCTG GAAAGACACT TACGGAGATA       480

AGCAAGCAAT TAAATTTGCC TAAGTCGTCT GTGCATGGGG TGATACAAAT TTTCAAAAAA       540

AATGGGAATA TTGAAAATAA CATTGCGAAT AGAGGCCGAA CATCAGCAAT AACACCCCGC       600

GACAAAAGAC AACTGGCCAA AATTGTTAAG GCTGATCGTC GCCAATCTTT GAGAAATTTG       660

GCTTCTAAGT GGTCGCAGCA ATTGGCAAAA CTGTCAAGCG AGAGTGGACG CGACAAATTA       720

AAAAGTATTG GATATGGTTT TTATAAAGTA TGTTTTGTTA TTACCTGTGC ATCGTACCCA       780

ATAACTTACT CGTAATCTTA CTCGTAGGCC AAGGAAAAAC CCTTGCTTAC GCTTCGTCAA       840

AAAAAGAAGC GTTTGCAATG GGCTCGGGAA AGGATGTCTT GGACTCAAAG GCAATGGGAT       900

ACCATCATAT TCAGCGATGA AGCTAAATTT GATGTTAGTG TCGGCGATAC GAGAAAACGC       960

GTCATCCGTA AGAGGTCAGA AACATACCAT AAAGACTGCC TTAAAAGAAC AACAAAGTTT      1020

CCTGCGAGCA CTATGGTATG GGGATGTATG TCTGCCAAAG GATTAGGAAA ACTTCATTTC      1080

ATTGAAGGGA CAGTTAATGC TGAAAAATAT ATTAATATTT TACAAGATAG TTTGTTGCCA      1140

TCAATACCAA AACTATCAGA TTGCGGTGAA TTCACTTTTC AGCAGGACGG AGCATCATCG      1200

CACACAGCCA AGCGAACCAA AAATTGGCTG CAATATAATC AAATGGAGGT TTTAGATTGG      1260

CCATCAAATA GTCCAGATCT AAGCCCAATT GAAAATATTT GGTGGCTAAT GAAAAACCAG      1320

CTTCGAAATG AGCCACAAAG GAATATTTCT GACTTGAAAA TCAAGTTGCA AGAGATGTGG      1380

GACTCAATTT CTCAAGAGCA TTGCAAAAAT TTGTTAAGCT CAATGCCAAA ACGAGTTAAA      1440
```

-continued

```
TGCGTAATGC AGGCCAAGGG CGACGTTACA CAATTCTAAT ATTAATTAAA TTATTGTTTT    1500

AAGTATGATA GTAAATCACA TTACGCCGCG TTCGAATTAA TAGTGGTCAC TTTTTTCTTA    1560

TCTCTTAAGC AAACCGTTTG AATAAATTAC TCATATTTTT GTTGTTGTTG GAAATAGAGC    1620

AAAACTTTTT TTTTCGTCGT GAAGAGAATA AAATTCTCTT TGAGACGAAA TGCATTGGTA    1680

TGTGTTATCT TTAGTAGTAT TGATAATATA GTGTGTTAAA CATTGCGCAC TGCAAAAAAA    1740

ACATGCTGTT CGAATTAATA GTGGTTGGGG CTCGT                               1775
```

(2) INFORMATION FOR SEQ ID NO:4:

(i) SEQUENCE CHARACTERISTICS:
        (A) LENGTH: 1779 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(398..751, 812..898)

(xi) SEQUENCE DESCRIPTION: SEQ ID NO:4:

```
ACGAGCCCCA ACCACTATTA ATTCGAACAG CATGTTTTTT TTGCAGTGCG CAATGTTTAA     60

CACACTATAT TATCAATACT ACTAAAGATA ACACATACCA ATGCATTTCG TCTCAAAGAG    120

AATTTTATTC TCTTCACGAC GAAAAAAAAA GTTTTGCTCT ATTCCAACA ACAACAAAAA     180

TATGAGTAAT TTATTCAAAC GGTTTGCTTA AGAGATAAGA AAAAAGTGAC CACTATTAAT    240

TCGAACGCGG CGTAAGCTTA CCTTAATCTC AAGAAGAGCA AAACAAAAGC AACTAATGTA    300

ACGGAATCAT TATCTAGTTA TGATCTGCAA ATAATGTCAC AATACAGCAT GCAAAAAAAT    360

TTTAGAATTG CTGCAGATCA GTAGAAGTTT AGCAACG ATG GTT CGT GGT AAA CCT    415
                                           Met Val Arg Gly Lys Pro
                                             1               5

ATT TCT AAA GAA ATC AGA GTA TTG ATT AGG GAT TAT TTT AAA TCT GGA      463
Ile Ser Lys Glu Ile Arg Val Leu Ile Arg Asp Tyr Phe Lys Ser Gly
         10                  15                  20

AAG ACA CTT ACG GAG ATA AGC AAG CAA TTA AAT TTG CCT AAG TCG TCT      511
Lys Thr Leu Thr Glu Ile Ser Lys Gln Leu Asn Leu Pro Lys Ser Ser
     25                  30                  35

GTG CAT GGG GTG ATA CAA ATT TTC AAA AAA AAT GGG AAT ATT GAA AAT      559
Val His Gly Val Ile Gln Ile Phe Lys Lys Asn Gly Asn Ile Glu Asn
 40                  45                  50

AAC ATT GCG AAT AGA GGC CGA ACA TCA GCA ATA ACA CCC CGC GAC AAA      607
Asn Ile Ala Asn Arg Gly Arg Thr Ser Ala Ile Thr Pro Arg Asp Lys
 55                  60                  65                  70

AGA CAA CTG GCC AAA ATT GTT AAG GCT GAT CGT CGC CAA TCT TTG AGA      655
Arg Gln Leu Ala Lys Ile Val Lys Ala Asp Arg Arg Gln Ser Leu Arg
             75                  80                  85

AAT TTG GCT TCT AAG TGG TCG CAG ACA ATT GGC AAA ACT GTC AAG CGA      703
Asn Leu Ala Ser Lys Trp Ser Gln Thr Ile Gly Lys Thr Val Lys Arg
         90                  95                 100

GAG TGG ACG CGA CAG CAA TTA AAA AGT ATT GGA TAT GGT TTT TAT AAA      751
Glu Trp Thr Arg Gln Gln Leu Lys Ser Ile Gly Tyr Gly Phe Tyr Lys
     105                 110                 115

GTATGTTTTG TTATTACCTG TGCATCGTAC CCAATAACTT ACTCGTAATC TTACTCGTAG    811

GCC AAG GAA AAA CCC TTG CTT ACG CTT CGT CAA AAA AAG AAG CGT TTG      859
Ala Lys Glu Lys Pro Leu Leu Thr Leu Arg Gln Lys Lys Lys Arg Leu
 120                 125                 130
```

```
CAA TGG GCT CGG GAA AGG ATG TCT TGG ACT CAA AGG CAA TAGGATACCA      908
Gln Trp Ala Arg Glu Arg Met Ser Trp Thr Gln Arg Gln
135                 140                 145

TCATATTCAG CGATGAAGCT AAATTTGATG TTAGTGTCGG CGATACGAGA AAACGCGTCA    968

TCCGTAAGAG GTCAGAAACA TACCATAAAG ACTGCCTTAA AGAACAACA AAGTTTCCTG    1028

CGAGCACTAT GGTATGGGGA TGTATGTCTG CCAAAGGATT AGGAAAACTT CATTTCATTG   1088

AAGGGACAGT TAATGCTGAA AAATATATTA ATATTTTACA AGATAGTTTG TTGCCATCAA   1148

TACCAAAACT ATCAGATTGC GGTGAATTCA CTTTTCAGCA GGACGGAGCA TCATCGCACA   1208

CAGCCAAGCG AACCAAAAAT TGGCTGCAAT ATAATCAAAT GGAGGTTTTA GATTGGCCAT   1268

CAAATAGTCC AGATCTAAGC CCAATTGAAA ATATTTGGTG GCTAATGAAA AACCAGCTTC   1328

GAAATGAGCC ACAAAGGAAT ATTTCTGACT TGAAAATCAA GTTGCAAGAG ATGTGGGACT   1388

CAATTTCTCA AGAGCATTGC AAAAATTTGT TAAGCTCAAT GCCAAAACGA GTTAAATGCG   1448

TAATGCAGGC CAAGGGCGAC GTTACACAAT TCTAATATTA ATTAAATTAT TGTTTTAAGT   1508

ATGATAGTAA ATCACATTAC GCCGCGTTCG AATTAATAGT GGTCACTTTT TTCTTATCTC   1568

TTAAGCAAAC CGTTTGAATA AATTACTCAT ATTTTTGTTG TTGTTGGAAA TAGAGCAAAA   1628

CTTTTTTTTT CGTCGTGAAG AGAATAAAAT TCTCTTTGAG ACGAAATGCA TTGGTATGTG   1688

TTATCTTTAG TAGTATTGAT AATATAGTGT GTTAAACATT GCGCACTGCA AAAAAAACAT   1748

GCTGTTCGAA TTAATAGTGG TTGGGGCTCG T                                  1779
```

(2) INFORMATION FOR SEQ ID NO:5:

(i) SEQUENCE CHARACTERISTICS:
        (A) LENGTH: 147 amino acids
        (B) TYPE: amino acid
        (D) TOPOLOGY: linear (ii) MOLECULE TYPE: protein (xi) SEQUENCE DESCRIPTION: SEQ ID NO:5:

```
Met Val Arg Gly Lys Pro Ile Ser Lys Glu Ile Arg Val Leu Ile Arg
  1               5                  10                  15

Asp Tyr Phe Lys Ser Gly Lys Thr Leu Thr Glu Ile Ser Lys Gln Leu
                 20                  25                  30

Asn Leu Pro Lys Ser Ser Val His Gly Val Ile Gln Ile Phe Lys Lys
             35                  40                  45

Asn Gly Asn Ile Glu Asn Asn Ile Ala Asn Arg Gly Arg Thr Ser Ala
         50                  55                  60

Ile Thr Pro Arg Asp Lys Arg Gln Leu Ala Lys Ile Val Lys Ala Asp
 65                  70                  75                  80

Arg Arg Gln Ser Leu Arg Asn Leu Ala Ser Lys Trp Ser Gln Thr Ile
                 85                  90                  95

Gly Lys Thr Val Lys Arg Glu Trp Thr Arg Gln Leu Lys Ser Ile
                100                 105                 110

Gly Tyr Gly Phe Tyr Lys Ala Lys Glu Lys Pro Leu Leu Thr Leu Arg
            115                 120                 125

Gln Lys Lys Lys Arg Leu Gln Trp Ala Arg Glu Arg Met Ser Trp Thr
        130                 135                 140

Gln Arg Gln
145
```

-continued (2) INFORMATION FOR SEQ ID NO:6:

(i) SEQUENCE CHARACTERISTICS:
        (A) LENGTH: 1779 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(398..751, 812..1480)

(xi) SEQUENCE DESCRIPTION: SEQ ID NO:6:

```
ACGAGCCCCA ACCACTATTA ATTCGAACAG CATGTTTTTT TTGCAGTGCG CAATGTTTAA       60

CACACTATAT TATCAATACT ACTAAAGATA ACACATACCA ATGCATTTCG TCTCAAAGAG      120

AATTTTATTC TCTTCACGAC GAAAAAAAAA GTTTTGCTCT ATTTCCAACA ACAACAAAAA      180

TATGAGTAAT TTATTCAAAC GGTTTGCTTA AGAGATAAGA AAAAGTGAC CACTATTAAT       240

TCGAACGCGG CGTAAGCTTA CCTTAATCTC AAGAAGAGCA AAACAAAAGC AACTAATGTA      300

ACGGAATCAT TATCTAGTTA TGATCTGCAA ATAATGTCAC AATACAGCAT GCAAAAAAAT      360

TTTAGAATTG CTGCAGATCA GTAGAAGTTT AGCAACG ATG GTT CGT GGT AAA CCT       415
                                        Met Val Arg Gly Lys Pro
                                          1               5

ATT TCT AAA GAA ATC AGA GTA TTG ATT AGG GAT TAT TTT AAA TCT GGA        463
Ile Ser Lys Glu Ile Arg Val Leu Ile Arg Asp Tyr Phe Lys Ser Gly
           10                  15                  20

AAG ACA CTT ACG GAG ATA AGC AAG CAA TTA AAT TTG CCT AAG TCG TCT        511
Lys Thr Leu Thr Glu Ile Ser Lys Gln Leu Asn Leu Pro Lys Ser Ser
         25                  30                  35

GTG CAT GGG GTG ATA CAA ATT TTC AAA AAA AAT GGG AAT ATT GAA AAT        559
Val His Gly Val Ile Gln Ile Phe Lys Lys Asn Gly Asn Ile Glu Asn
     40                  45                  50

AAC ATT GCG AAT AGA GGC CGA ACA TCA GCA ATA ACA CCC CGC GAC AAA        607
Asn Ile Ala Asn Arg Gly Arg Thr Ser Ala Ile Thr Pro Arg Asp Lys
 55                  60                  65                  70

AGA CAA CTG GCC AAA ATT GTT AAG GCT GAT CGT CGC CAA TCT TTG AGA        655
Arg Gln Leu Ala Lys Ile Val Lys Ala Asp Arg Arg Gln Ser Leu Arg
             75                  80                  85

AAT TTG GCT TCT AAG TGG TCG CAG ACA ATT GGC AAA ACT GTC AAG CGA        703
Asn Leu Ala Ser Lys Trp Ser Gln Thr Ile Gly Lys Thr Val Lys Arg
         90                  95                 100

GAG TGG ACG CGA CAG CAA TTA AAA AGT ATT GGA TAT GGT TTT TAT AAA        751
Glu Trp Thr Arg Gln Gln Leu Lys Ser Ile Gly Tyr Gly Phe Tyr Lys
        105                 110                 115

GTATGTTTTG TTATTACCTG TGCATCGTAC CCAATAACTT ACTCGTAATC TTACTCGTAG      811

GCC AAG GAA AAA CCC TTG CTT ACG CTT CGT CAA AAA AAG AAG CGT TTG        859
Ala Lys Glu Lys Pro Leu Leu Thr Leu Arg Gln Lys Lys Lys Arg Leu
        120                 125                 130

CAA TGG GCT CGG GAA AGG ATG TCT TGG ACT CAA AGG CAA TGG GAT ACC        907
Gln Trp Ala Arg Glu Arg Met Ser Trp Thr Gln Arg Gln Trp Asp Thr
135                 140                 145                 150

ATC ATA TTC AGC GAT GAA GCT AAA TTT GAT GTT AGT GTC GGC GAT ACG        955
Ile Ile Phe Ser Asp Glu Ala Lys Phe Asp Val Ser Val Gly Asp Thr
                155                 160                 165

AGA AAA CGC GTC ATC CGT AAG AGG TCA GAA ACA TAC CAT AAA GAC TGC       1003
Arg Lys Arg Val Ile Arg Lys Arg Ser Glu Thr Tyr His Lys Asp Cys
            170                 175                 180
```

```
CTT AAA AGA ACA ACA AAG TTT CCT GCG AGC ACT ATG GTA TGG GGA TGT    1051
Leu Lys Arg Thr Thr Lys Phe Pro Ala Ser Thr Met Val Trp Gly Cys
        185                 190                 195

ATG TCT GCC AAA GGA TTA GGA AAA CTT CAT TTC ATT GAA GGG ACA GTT    1099
Met Ser Ala Lys Gly Leu Gly Lys Leu His Phe Ile Glu Gly Thr Val
200                 205                 210

AAT GCT GAA AAA TAT ATT AAT ATT TTA CAA GAT AGT TTG TTG CCA TCA    1147
Asn Ala Glu Lys Tyr Ile Asn Ile Leu Gln Asp Ser Leu Leu Pro Ser
215                 220                 225                 230

ATA CCA AAA CTA TTA GAT TGC GGT GAA TTC ACT TTT CAG CAG GAC GGA    1195
Ile Pro Lys Leu Leu Asp Cys Gly Glu Phe Thr Phe Gln Gln Asp Gly
            235                 240                 245

GCA TCA TCG CAC ACA GCC AAG CGA ACC AAA AAT TGG CTG CAA TAT AAT    1243
Ala Ser Ser His Thr Ala Lys Arg Thr Lys Asn Trp Leu Gln Tyr Asn
                250                 255                 260

CAA ATG GAG GTT TTA GAT TGG CCA TCA AAT AGT CCA GAT CTA AGC CCA    1291
Gln Met Glu Val Leu Asp Trp Pro Ser Asn Ser Pro Asp Leu Ser Pro
            265                 270                 275

ATT GAA AAT ATT TGG TGG CTA ATG AAA AAC CAG CTT CGA AAT GAG CCA    1339
Ile Glu Asn Ile Trp Trp Leu Met Lys Asn Gln Leu Arg Asn Glu Pro
280                 285                 290

CAA AGG AAT ATT TCT GAC TTG AAA ATC AAG TTG CAA GAG ATG TGG GAC    1387
Gln Arg Asn Ile Ser Asp Leu Lys Ile Lys Leu Gln Glu Met Trp Asp
295                 300                 305                 310

TCA ATT TCT CAA GAG CAT TGC AAA AAT TTG TTA AGC TCA ATG CCA AAA    1435
Ser Ile Ser Gln Glu His Cys Lys Asn Leu Leu Ser Ser Met Pro Lys
                315                 320                 325

CGA GTT AAA TGC GTA ATG CAG GCC AAG GGC GAC GTT ACA CAA TTC         1480
Arg Val Lys Cys Val Met Gln Ala Lys Gly Asp Val Thr Gln Phe
            330                 335                 340

TAATATTAAT TAAATTATTG TTTTAAGTAT GATAGTAAAT CACATTACGC CGCGTTCGAA   1540

TTAATAGTGG TCACTTTTTT CTTATCTCTT AAGCAAACCG TTTGAATAAA TTACTCATAT   1600

TTTTGTTGTT GTTGGAAATA GAGCAAAACT TTTTTTTTCG TCGTGAAGAG AATAAAATTC   1660

TCTTTGAGAC GAAATGCATT GGTATGTGTT ATCTTTAGTA GTATTGATAA TATAGTGTGT   1720

TAAACATTGC GCACTGCAAA AAAAACATGC TGTTCGAATT AATAGTGGTT GGGGCTCGT    1779
```

(2) INFORMATION FOR SEQ ID NO:7:

(i) SEQUENCE CHARACTERISTICS:
        (A) LENGTH: 341 amino acids
        (B) TYPE: amino acid
        (D) TOPOLOGY: linear (ii) MOLECULE TYPE: protein (xi) SEQUENCE DESCRIPTION: SEQ ID NO:7:

```
Met Val Arg Gly Lys Pro Ile Ser Lys Glu Ile Arg Val Leu Ile Arg
1               5                   10                  15

Asp Tyr Phe Lys Ser Gly Lys Thr Leu Thr Glu Ile Ser Lys Gln Leu
            20                  25                  30

Asn Leu Pro Lys Ser Ser Val His Gly Val Ile Gln Ile Phe Lys Lys
        35                  40                  45

Asn Gly Asn Ile Glu Asn Asn Ile Ala Asn Arg Gly Arg Thr Ser Ala
    50                  55                  60

Ile Thr Pro Arg Asp Lys Arg Gln Leu Ala Lys Ile Val Lys Ala Asp
65                  70                  75                  80

Arg Arg Gln Ser Leu Arg Asn Leu Ala Ser Lys Trp Ser Gln Thr Ile
                85                  90                  95
```

```
Gly Lys Thr Val Lys Arg Glu Trp Thr Arg Gln Gln Leu Lys Ser Ile
            100                 105                 110
Gly Tyr Gly Phe Tyr Lys Ala Lys Glu Lys Pro Leu Leu Thr Leu Arg
        115                 120                 125
Gln Lys Lys Arg Leu Gln Trp Ala Arg Glu Arg Met Ser Trp Thr
130                 135                 140
Gln Arg Gln Trp Asp Thr Ile Ile Phe Ser Asp Glu Ala Lys Phe Asp
145                 150                 155                 160
Val Ser Val Gly Asp Thr Arg Lys Arg Val Ile Arg Lys Arg Ser Glu
                165                 170                 175
Thr Tyr His Lys Asp Cys Leu Lys Arg Thr Lys Phe Pro Ala Ser
            180                 185                 190
Thr Met Val Trp Gly Cys Met Ser Ala Lys Gly Leu Gly Lys Leu His
        195                 200                 205
Phe Ile Glu Gly Thr Val Asn Ala Glu Lys Tyr Ile Asn Ile Leu Gln
    210                 215                 220
Asp Ser Leu Leu Pro Ser Ile Pro Lys Leu Leu Asp Cys Gly Glu Phe
225                 230                 235                 240
Thr Phe Gln Gln Asp Gly Ala Ser Ser His Thr Ala Lys Arg Thr Lys
                245                 250                 255
Asn Trp Leu Gln Tyr Asn Gln Met Glu Val Leu Asp Trp Pro Ser Asn
            260                 265                 270
Ser Pro Asp Leu Ser Pro Ile Glu Asn Ile Trp Trp Leu Met Lys Asn
        275                 280                 285
Gln Leu Arg Asn Glu Pro Gln Arg Asn Ile Ser Asp Leu Lys Ile Lys
    290                 295                 300
Leu Gln Glu Met Trp Asp Ser Ile Ser Gln Glu His Cys Lys Asn Leu
305                 310                 315                 320
Leu Ser Ser Met Pro Lys Arg Val Lys Cys Val Met Gln Ala Lys Gly
                325                 330                 335
Asp Val Thr Gln Phe
            340

(2) INFORMATION FOR SEQ ID NO:8:

(i) SEQUENCE CHARACTERISTICS:
        (A) LENGTH: 1779 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: join(398..751, 812..1480)

(xi) SEQUENCE DESCRIPTION: SEQ ID NO:8:

ACGAGCCCCA ACCACTATTA ATTCGAACAG CATGTTTTTT TTGCAGTGCG CAATGTTTAA      60

CACACTATAT TATCAATACT ACTAAAGATA ACACATACCA ATGCATTTCG TCTCAAAGAG     120

AATTTTATTC TCTTCACGAC GAAAAAAAAA GTTTTGCTCT ATTTCCAACA CAACAAAAA     180

TATGAGTAAT TTATTCAAAC GGTTTGCTTA AGAGATAAGA AAAAGTGAC CACTATTAAT     240

TCGAACGCGG CGTAAGCTTA CCTTAATCTC AAGAAGAGCA AAACAAAAGC AACTAATGTA     300

ACGGAATCAT TATCTAGTTA TGATCTGCAA ATAATGTCAC AATACAGCAT GCAAAAAAAT     360
```

-continued

| | |
|---|---|
| TTTAGAATTG CTGCAGATCA GTAGAAGTTT AGCAACG ATG GTT CGT GGT AAA CCT<br>                                                                   Met Val Arg Gly Lys Pro<br>                                                                    1                5 | 415 |
| ATT TCT AAA GAA ATC AGA GTA TTG ATT AGG GAT TAT TTT AAA TCT GGA<br>Ile Ser Lys Glu Ile Arg Val Leu Ile Arg Asp Tyr Phe Lys Ser Gly<br>              10                    15                        20 | 463 |
| AAG ACA CTT ACG GAG ATA AGC AAG CAA TTA AAT TTG CCT AAG TCG TCT<br>Lys Thr Leu Thr Glu Ile Ser Lys Gln Leu Asn Leu Pro Lys Ser Ser<br>           25                       30                         35 | 511 |
| GTG CAT GGG GTG ATA CAA ATT TTC AAA AAA AAT GGG AAT ATT GAA AAT<br>Val His Gly Val Ile Gln Ile Phe Lys Lys Asn Gly Asn Ile Glu Asn<br> 40                         45                         50 | 559 |
| AAC ATT GCG AAT AGA GGC CGA ACA TCA GCA ATA ACA CCC CGC GAC AAA<br>Asn Ile Ala Asn Arg Gly Arg Thr Ser Ala Ile Thr Pro Arg Asp Lys<br>55                  60                    65                     70 | 607 |
| AGA CAA CTG GCC AAA ATT GTT AAG GCT GAT CGT CGC CAA TCT TTG AGA<br>Arg Gln Leu Ala Lys Ile Val Lys Ala Asp Arg Arg Gln Ser Leu Arg<br>           75                       80                     85 | 655 |
| AAT TTG GCT TCT AAG TGG TCG CAG ACA ATT GGC AAA ACT GTC AAG CGA<br>Asn Leu Ala Ser Lys Trp Ser Gln Thr Ile Gly Lys Thr Val Lys Arg<br>             90                    95                   100 | 703 |
| GAG TGG ACG CGA CAG CAA TTA AAA AGT ATT GGA TAT GGT TTT TAT AAA<br>Glu Trp Thr Arg Gln Gln Leu Lys Ser Ile Gly Tyr Gly Phe Tyr Lys<br>          105                    110                  115 | 751 |
| GTATGTTTTG TTATTACCTG TGCATCGTAC CCAATAACTT ACTCGTAATC TTACTCGTAG | 811 |
| GCC AAG GAA AAA CCC TTG CTT ACG CTT CGT CAA AAA AAG AAG CGT TTG<br>Ala Lys Glu Lys Pro Leu Leu Thr Leu Arg Gln Lys Lys Lys Arg Leu<br>120                  125                     130 | 859 |
| CAA TGG GCT CGG GAA AGG ATG TCT TGG ACT CAA AGG CAA TGG GAT ACC<br>Gln Trp Ala Arg Glu Arg Met Ser Trp Thr Gln Arg Gln Trp Asp Thr<br>135                  140                     145                 150 | 907 |
| ATC ATA TTC AGC GAT GAA GCT AAA TTT GAT GTT AGT GTC GGC GAT ACG<br>Ile Ile Phe Ser Asp Glu Ala Lys Phe Asp Val Ser Val Gly Asp Thr<br>           155                    160                  165 | 955 |
| AGA AAA CGC GTC ATC CGT AAG AGG TCA GAA ACA TAC CAT AAA GAC TGC<br>Arg Lys Arg Val Ile Arg Lys Arg Ser Glu Thr Tyr His Lys Asp Cys<br>           170                    175                  180 | 1003 |
| CTT AAA AGA ACA ACA AAG TTT CCT GCG AGC ACT ATG GTA TGG GGA TGT<br>Leu Lys Arg Thr Thr Lys Phe Pro Ala Ser Thr Met Val Trp Gly Cys<br>           185                    190                  195 | 1051 |
| ATG TCT GCC AAA GGA TTA GGA AAA CTT CAT TTC ATT GAA GGG ACA GTT<br>Met Ser Ala Lys Gly Leu Gly Lys Leu His Phe Ile Glu Gly Thr Val<br>200                  205                     210 | 1099 |
| AAT GCT GAA AAA TAT ATT AAT ATT TTA CAA GAT AGT TTG TTG CCA TCA<br>Asn Ala Glu Lys Tyr Ile Asn Ile Leu Gln Asp Ser Leu Leu Pro Ser<br>215                  220                     225                 230 | 1147 |
| ATA CCA AAA CTA TCA GAT TGC GGT GAA TTC ACT TTT CAG CAG GAC GGA<br>Ile Pro Lys Leu Ser Asp Cys Gly Glu Phe Thr Phe Gln Gln Asp Gly<br>                 235                    240                  245 | 1195 |
| GCA TCA TCG CAC ACA GCC AAG CGA ACC AAA AAT TGG CTG CAA TAT AAT<br>Ala Ser Ser His Thr Ala Lys Arg Thr Lys Asn Trp Leu Gln Tyr Asn<br>           250                    255                  260 | 1243 |
| CAA ATG GAG GTT TTA GAT TGG CCA TCA AAT AGT CCA GAT CTA AGC CCA<br>Gln Met Glu Val Leu Asp Trp Pro Ser Asn Ser Pro Asp Leu Ser Pro<br>265                  270                     275 | 1291 |
| ATT GAA AAT ATT TGG TGG CTA ATG AAA AAC CAG CTT CGA AAT GAG CCA<br>Ile Glu Asn Ile Trp Trp Leu Met Lys Asn Gln Leu Arg Asn Glu Pro<br>           280                    285                  290 | 1339 |

```
CAA AGG AAT ATT TCT GAC TTG AAA ATC AAG TTG CAA GAG ATG TGG GAC       1387
Gln Arg Asn Ile Ser Asp Leu Lys Ile Lys Leu Gln Glu Met Trp Asp
295                 300                 305                 310

TCA ATT TCT CAA GAG CAT TGC AAA AAT TTG TTA AGC TCA ATG CCA AAA       1435
Ser Ile Ser Gln Glu His Cys Lys Asn Leu Leu Ser Ser Met Pro Lys
            315                 320                 325

CGA GTT AAA TGC GTA ATG CAG GCC AAG GGC GAC GTT ACA CAA TTC           1480
Arg Val Lys Cys Val Met Gln Ala Lys Gly Asp Val Thr Gln Phe
        330                 335                 340

TAATATTAAT TAAATTATTG TTTTAAGTAT GATAGTAAAT CACATTACGC CGCGTTCGAA     1540

TTAATAGTGG TCACTTTTTT CTTATCTCTT AAGCAAACCG TTTGAATAAA TTACTCATAT     1600

TTTTGTTGTT GTTGGAAATA GAGCAAAACT TTTTTTTTCG TCGTGAAGAG AATAAAATTC     1660

TCTTTGAGAC GAAATGCATT GGTATGTGTT ATCTTTAGTA GTATTGATAA TATAGTGTGT     1720

TAAACATTGC GCACTGCAAA AAAAACATGC TGTTCGAATT AATAGTGGTT GGGGCTCGT      1779

(2) INFORMATION FOR SEQ ID NO:9:

(i) SEQUENCE CHARACTERISTICS:
        (A) LENGTH: 341 amino acids
        (B) TYPE: amino acid
        (D) TOPOLOGY: linear (ii) MOLECULE TYPE: protein (xi) SEQUENCE DESCRIPTION: SEQ ID NO:9:

Met Val Arg Gly Lys Pro Ile Ser Lys Glu Ile Arg Val Leu Ile Arg
1               5                   10                  15

Asp Tyr Phe Lys Ser Gly Lys Thr Leu Thr Glu Ile Ser Lys Gln Leu
                20                  25                  30

Asn Leu Pro Lys Ser Ser Val His Gly Val Ile Gln Ile Phe Lys Lys
            35                  40                  45

Asn Gly Asn Ile Glu Asn Asn Ile Ala Asn Arg Gly Arg Thr Ser Ala
        50                  55                  60

Ile Thr Pro Arg Asp Lys Arg Gln Leu Ala Lys Ile Val Lys Ala Asp
65                  70                  75                  80

Arg Arg Gln Ser Leu Arg Asn Leu Ala Ser Lys Trp Ser Gln Thr Ile
                85                  90                  95

Gly Lys Thr Val Lys Arg Glu Trp Thr Arg Gln Leu Lys Ser Ile
                100                 105                 110

Gly Tyr Gly Phe Tyr Lys Ala Lys Glu Lys Pro Leu Leu Thr Leu Arg
            115                 120                 125

Gln Lys Lys Lys Arg Leu Gln Trp Ala Arg Glu Arg Met Ser Trp Thr
130                 135                 140

Gln Arg Gln Trp Asp Thr Ile Ile Phe Ser Asp Glu Ala Lys Phe Asp
145                 150                 155                 160

Val Ser Val Gly Asp Thr Arg Lys Arg Val Ile Arg Lys Arg Ser Glu
                165                 170                 175

Thr Tyr His Lys Asp Cys Leu Lys Arg Thr Thr Lys Phe Pro Ala Ser
            180                 185                 190

Thr Met Val Trp Gly Cys Met Ser Ala Lys Gly Leu Gly Lys Leu His
        195                 200                 205

Phe Ile Glu Gly Thr Val Asn Ala Glu Lys Tyr Ile Asn Ile Leu Gln
210                 215                 220

Asp Ser Leu Leu Pro Ser Ile Pro Lys Leu Ser Asp Cys Gly Glu Phe
225                 230                 235                 240
```

```
Thr Phe Gln Gln Asp Gly Ala Ser Ser His Thr Ala Lys Arg Thr Lys
            245                 250                 255

Asn Trp Leu Gln Tyr Asn Gln Met Glu Val Leu Asp Trp Pro Ser Asn
            260                 265                 270

Ser Pro Asp Leu Ser Pro Ile Glu Asn Ile Trp Trp Leu Met Lys Asn
            275                 280                 285

Gln Leu Arg Asn Glu Pro Gln Arg Asn Ile Ser Asp Leu Lys Ile Lys
            290                 295                 300

Leu Gln Glu Met Trp Asp Ser Ile Ser Gln Glu His Cys Lys Asn Leu
305                 310                 315                 320

Leu Ser Ser Met Pro Lys Arg Val Lys Cys Val Met Gln Ala Lys Gly
            325                 330                 335

Asp Val Thr Gln Phe
            340
```

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

```
Met Val Trp Gly Cys
1               5
```

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

```
Trp Pro Ser Gln Ser Pro Asp Leu
1               5
```

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

```
Trp Pro Ser Asn Ser Pro Asp Leu
1               5
```